United States Patent
Black et al.

(10) Patent No.: US 10,058,359 B2
(45) Date of Patent: Aug. 28, 2018

(54) ANCHOR ASSEMBLY TOOLS, KITS, AND METHODS

(71) Applicant: DeGen Medical, Inc., Florence, SC (US)

(72) Inventors: Craig Black, Florence, SC (US); Hitesh Mehta, Florence, SC (US); Kidong Yu, Florence, SC (US)

(73) Assignee: DeGen Medical, Inc., Florence, SC (US)

( * ) Notice: Subject to any disclaimer, the term of this patent is extended or adjusted under 35 U.S.C. 154(b) by 262 days.

(21) Appl. No.: 14/951,550

(22) Filed: Nov. 25, 2015

(65) Prior Publication Data

US 2016/0143672 A1     May 26, 2016

Related U.S. Application Data

(60) Provisional application No. 62/084,958, filed on Nov. 26, 2014.

(51) Int. Cl.
    *B23Q 1/00*              (2006.01)
    *A61B 17/70*            (2006.01)
    *F16B 25/00*            (2006.01)

(52) U.S. Cl.
    CPC ........ *A61B 17/7076* (2013.01); *F16B 25/001* (2013.01)

(58) Field of Classification Search
    USPC ............... 29/282, 283, 283.5; 606/86 A, 278
    See application file for complete search history.

(56) References Cited

U.S. PATENT DOCUMENTS

| | | | |
|---|---|---|---|
| 8,048,124 B2 | 11/2011 | Chin et al. | |
| 8,308,774 B2 | 11/2012 | Hoffman et al. | |
| 8,747,411 B2 | 6/2014 | Mitchell | |
| 8,821,506 B2 | 9/2014 | Mitchell | |
| 9,649,140 B1 * | 5/2017 | Doose | A61B 17/708 |
| 9,757,166 B1 * | 9/2017 | Arnold | A61B 17/708 |

(Continued)

OTHER PUBLICATIONS

European Patent Office, Communication pursuant to Rules 161(1) and 162 EPC, dated Jul. 4, 2017, p. 1-2.

(Continued)

*Primary Examiner* — Joseph J Hail
*Assistant Examiner* — Shantese McDonald
(74) *Attorney, Agent, or Firm* — Buchanan Van Tuinen LLC

(57) ABSTRACT

The technical description relates to anchor assembly tools, drivers kits, and methods useful in connecting a structure with another structure. An anchor assembly tool includes an outer member having a distal end configured to engage a head member and an inner member having a distal end configured to engage an anchor. A driver includes an outer member, an inner member, and a grasping member. A set screw driver includes an outer member and an inner member. An example kit includes an anchor assembly tool, an anchor, and a head member. A method of assembling an anchor assembly tool comprises releasably attaching a head member to the distal end of the outer member, releasably attaching an anchor to the distal end of the inner member, and advancing the inner member within the outer member such that the anchor is disposed within the head member.

13 Claims, 20 Drawing Sheets

(56) References Cited

U.S. PATENT DOCUMENTS

| | | |
|---|---|---|
| 2006/0149291 A1 | 7/2006 | Selover |
| 2010/0030135 A1 | 2/2010 | Mitchell |
| 2010/0312251 A1 | 12/2010 | Landreneau |
| 2011/0245881 A1 | 10/2011 | Mitchell |
| 2013/0065698 A1 | 3/2013 | Biedermann et al. |
| 2014/0052138 A1 | 2/2014 | Kemper et al. |
| 2014/0107708 A1* | 4/2014 | Biedermann ...... A61B 17/7082 606/278 |
| 2014/0188175 A1 | 7/2014 | Mishra et al. |
| 2014/0276894 A1 | 9/2014 | Ramsay et al. |

OTHER PUBLICATIONS

International Searching Authority, International Search Report and Written Opinion, for Intl. App. No. PCT/U2015/062578, dated Mar. 4, 2016, pp. 1-13.

International Bureau of WIPO; International Preliminary Report on Patentability; International Application No. PCT/US2015/062578; dated May 30, 2017.

* cited by examiner

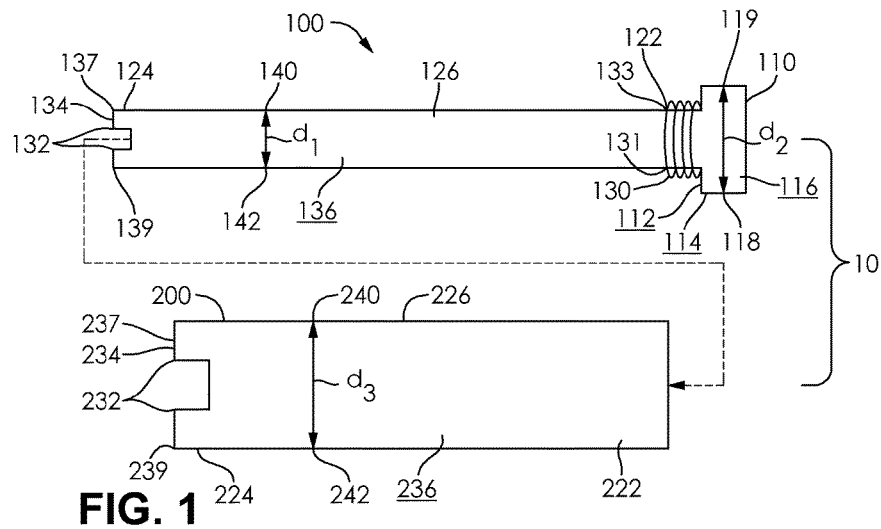
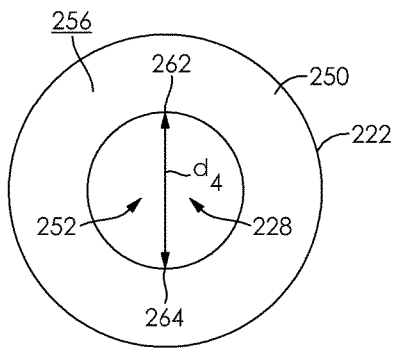
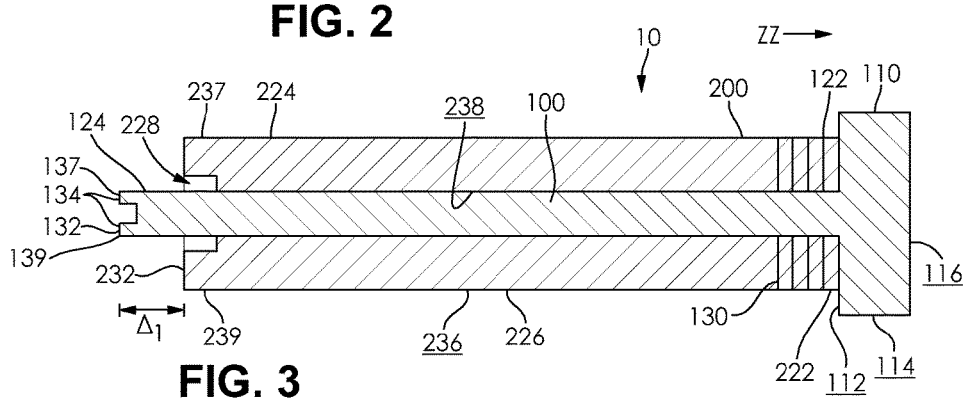
FIG. 1
FIG. 2
FIG. 3

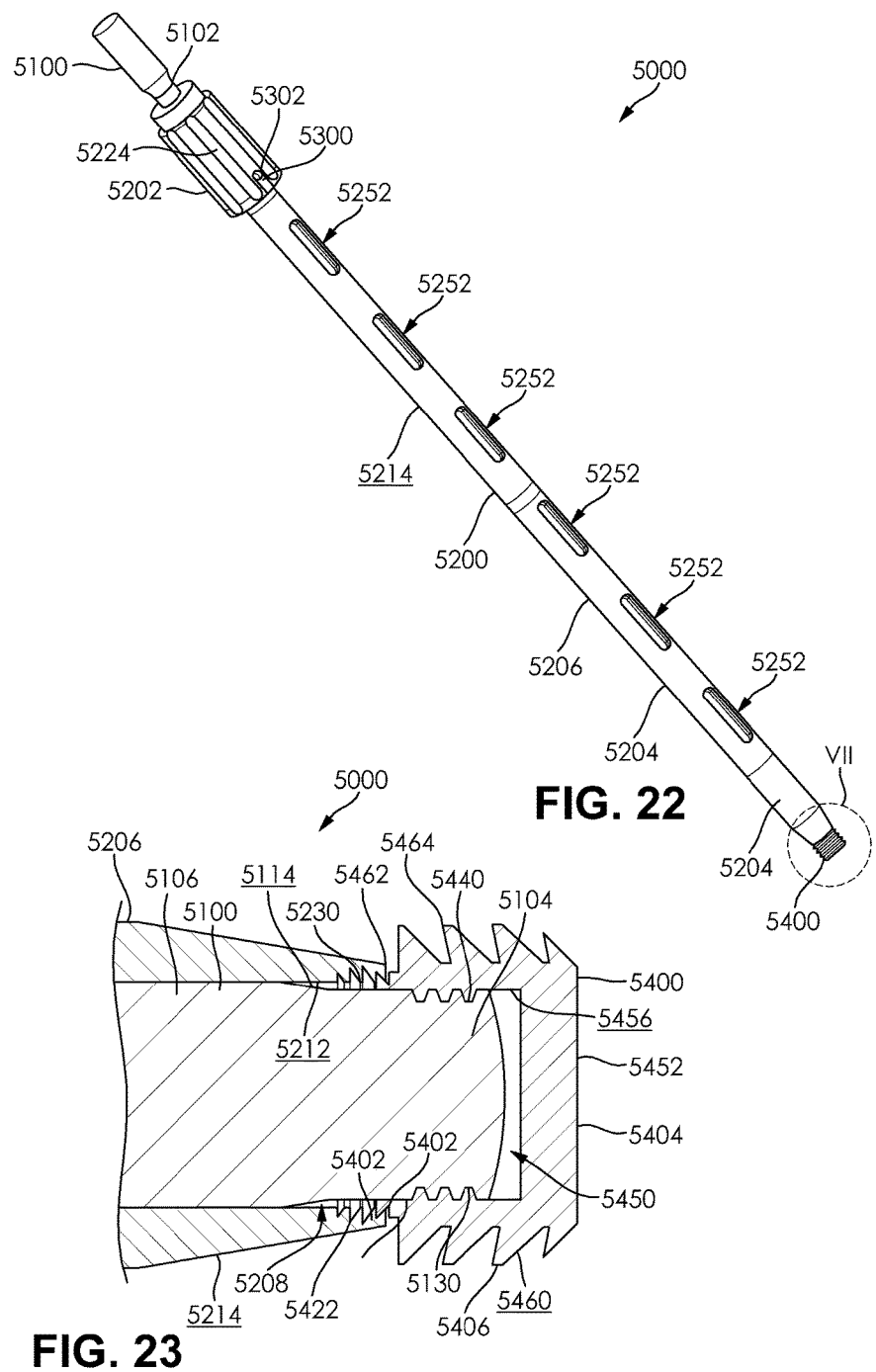

ANCHOR ASSEMBLY TOOLS, KITS, AND METHODS

RELATED APPLICATION

This application claims the benefit of U.S. Provisional Application No. 62/084,958 filed on Nov. 26, 2014. This related application is hereby incorporated into this disclosure in its entirety.

FIELD

The disclosure relates to the field of anchors useful for connecting structures to each other. More particularly, the disclosure relates to anchor-related tools, such as assembly tools useful for assembling anchor components. Specific examples relate to the field of bone anchors.

BACKGROUND

The art includes several examples of anchor-related tools useful for assembling anchor components and other anchor-related purposes. The medical device field, for example, includes anchor assembly tools useful for connecting a bone screw with a head member.

One such tool, described in U.S. Pat. No. 8,048,124 to Grant for SPINAL SCREW ASSEMBLY AND SCREW INSERTION TOOL, includes an elongated cylindrical driver shaft, a cylindrical retention sleeve, and an outer sleeve surrounding the retention sleeve. The distal end of the driver shaft is dimensioned to interface and engage with either a locking element or the top of a screw head.

Despite this and other examples, a need exists for improved anchor assembly tools, kits, and methods of assembling anchor components.

BRIEF SUMMARY OF SELECTED EXAMPLES

Various example anchor-related tools, kits, and methods are described and illustrated herein.

An example anchor assembly tool configured to engage a head member and an anchor comprises an outer member having an elongate, tubular main body, a proximal end, a distal end, a longitudinal axis, and a lumen extending from the proximal end to the distal end, the distal end configured to be releasably attached to said head member; and an inner member having an elongate, tubular main body and an actuator, the main body having a proximal end and a distal end, the inner member movably disposed within the lumen of the outer member, the actuator capable of advancing the inner member within the outer member, the actuator disposed on the proximal end of the main body, the distal end configured to be releasably attached to said anchor; the distal end of the outer member operates independently from the distal end of the inner member; and activation of the actuator moves the inner member a predetermined distance relative to the longitudinal axis from a first configuration to a second configuration.

Another example anchor assembly tool configured to engage a head member and an anchor comprises an outer member having an elongate, tubular main body, a proximal end, a distal end, a longitudinal axis, and a lumen extending from the proximal end to the distal end, the distal end defining a first threaded portion configured to engage a head member, the outer member rotatable about the longitudinal axis; and an inner member having an elongate, tubular main body and an actuator, the main body having a proximal end and a distal end, the inner member movably disposed within the lumen of the outer member, the actuator capable of advancing the inner member within the outer member, the actuator disposed on the proximal end of the main body, the distal end defining a second threaded portion configured to engage an anchor, the inner member rotatable about the longitudinal axis; the distal end of the outer member operates independently from the distal end of the inner member; and activation of the actuator moves the inner member a predetermined distance relative to the longitudinal axis from a first configuration to a second configuration Another example anchor assembly tool configured to engage a head member and an anchor defining a recess comprises an outer member having an elongate, tubular main body, a proximal end, a distal end, a longitudinal axis, a lumen extending from the proximal end to the distal end, and an outer member collar disposed on the elongate, tubular main body, the distal end defining a first threaded portion configured to engage the head member, the outer member rotatable about the longitudinal axis; an inner member having an elongate, tubular main body, a lumen, an inner shaft disposed within the lumen, and an actuator, the main body having a proximal end and a distal end, the inner member movably disposed within the lumen of the outer member, the actuator capable of advancing the inner member within the outer member, the actuator disposed on the proximal end of the main body, the inner shaft having a first position and a second position, the inner member having a radially compressed configuration relative to the longitudinal axis when the inner shaft is in the first position, the inner member having a radially expanded configuration relative to the longitudinal axis when the inner shaft is in the compressed position, the distal end defining a snap-fit structure, the snap-fit structure being configured to engage the anchor; and a handle having a first handle portion and a second handle portion, the first handle portion attached to the outer member, the second handle portion attached to the inner member, the handle having a first configuration and a second configuration; the distal end of the outer member operates independently from the distal end of the inner member; and activation of the handle from the first configuration to the second configuration moves the inner member a predetermined distance relative to the longitudinal axis.

Additional understanding of claimed anchor assembly tools can be obtained by reviewing the detailed description of selected examples, below, with reference to the appended drawings.

DESCRPTION OF FIGURES

FIG. 1 is an exploded view of a first example anchor assembly tool.

FIG. 2 is a magnified proximal end view of the outer member of the anchor assembly tool illustrated in FIG. 1.

FIG. 3 is a lengthwise cross-sectional view of the anchor assembly tool illustrated in FIG. 1. The anchor assembly tool is illustrated in a first configuration.

FIG. 22 is a perspective view of the set screw driver illustrated in FIG. 19 and an associated set screw.

FIG. 23 is a magnified lengthwise cross-sectional view of Area VII of the set screw driver and set screw illustrated in FIG. 22. The set screw is releasably attached to the set screw driver in this illustration.

DETAILED DESCRPTION OF SELECTED EXAMPLES

Figure 4:
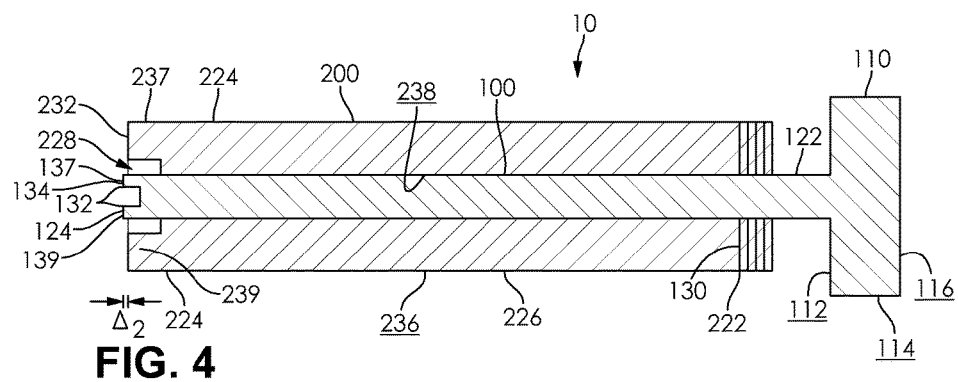
FIG. 4 is a lengthwise cross-sectional view of the anchor assembly tool illustrated in FIG. 1. The anchor assembly tool is illustrated in a second configuration.

The following detailed description and the appended drawings describe and illustrate various example anchor assembly tools, kits, and methods. The description and illustration of these examples are provided to enable one skilled in the art to make and use anchor assembly tools and kits, and to perform related methods. They are not intended to limit the scope of the claims in any manner.

Each of FIGS. 1, 2, 3, and 4 illustrates an anchor assembly tool 10 or one or more components thereof. The anchor assembly tool 10 includes an inner member 100 and an outer member 200. Inner member 100 is movably disposed within outer member 200.

The inner member 100 has an actuator 110, and a main body 126 comprising a proximal end 122, a distal end 124, an outer surface 136, and a spring 130. The distal end 124 has a distal tip 134.

In the illustrated embodiment, main body 126 is elongate and tubular and defines a first diameter $d_1$ extending directly from a first outer point 140 of the outer surface 136 to a second outer point 142 of the outer surface 136 substantially opposite the first outer point 140 about the longitudinal axis of the inner member 100. The main body 126 is substantially rectangular in cross-sectional shape and is uniform in diameter along its length. It is noted, though, that the main body may have other cross-sectional shapes in alternative embodiments, including rectangular, elliptical, and substantially elliptical. A skilled artisan will be to determine a suitable diameter and cross-sectional shape for the main body according to a particular example based on various considerations, including the shape and size of the outer member and the shape and size of the actuator. Additionally, in another embodiment the main body may define a non-uniform diameter. For example, in one particular embodiment the main body may define a first diameter at the proximal end and a second, smaller diameter at the distal end, thus providing the main body with a distal taper.

The actuator 110 is disposed adjacent the proximal end 122 of the main body 126. The actuator 110 defines an upper surface 116, a middle surface 114, and a lower surface 112. The lower surface 112 is substantially opposite the upper surface 116 about the middle surface 114. The actuator 110 is substantially rectangular in cross-sectional shape. In other embodiments, however, the actuator may have any cross-sectional shape, including rectangular, elliptical, and substantially elliptical. A skilled artisan will be to determine a suitable diameter and cross-sectional shape for the actuator according to a particular example based on various considerations, including the shape and size of the outer member and the shape and size of the main body. The actuator may also be disposed about along a portion of the main body in another embodiment.

The actuator 110 also defines a second diameter $d_2$ extending directly from a first outer point 118 of the middle surface 114 to a second outer point 119 of the middle surface 114 opposite the first outer point 118 about the longitudinal axis of the main body 126. The second diameter $d_2$ is greater than the first diameter $d_1$ in the illustrated embodiment. A skilled artisan will be able to determine a suitable second diameter according to a particular example based on various considerations, including the shape and size of the outer member and the shape and size of the main body. In alternative embodiments, the second diameter may be equal to, substantially equal to, or less than the first diameter.

Additionally, in the illustrated embodiment, the actuator 110 is welded onto the proximal end 122 of the main body 126 of the inner member 120. It is noted that the actuator 110 may be attached to the proximal end 122 in any suitable manner, however. A skilled artisan will be able to determine whether the actuator should be formed integrally with the main body and, if not, how to attach the actuator to the main body according to a particular example based on various considerations, including the shape and size of the outer member and the shape and size of the actuator. In other embodiments the actuator may be attached to the proximal end of the main body by one or more adhesives, suturing, one or more hooks, or any other suitable technique. In an alternative embodiment, the actuator may be integrally formed with the main body.

The spring 130 is attached to the proximal end 122 of the main body 126 and is adjacent the actuator 110. In the illustrated embodiment, the spring 130 is attached to the proximal end 122 at a first point 131 and a second point 133 such that the spring is still compressible. The spring 130 may be attached to the main body in any suitable manner, however. A skilled artisan will be able to determine a mechanism for attaching the spring to the main body according to a particular example based on various considerations, including the shape and size of the outer member and the shape and size of the main body. The spring may be welded to the proximal end at one, three, or more than three welding points in other embodiments. Alternatively, the spring may be attached to the proximal end by one or more adhesives, a hook or anchor, a pin, or any other mechanism of attachment.

The distal end 124 has a distal tip 134 and defines a first snap-fit structure 132 extending proximally from the distal tip 134. The first snap-fit structure 132 is configured to cooperatively mate with an anchor (not illustrated in FIGS. 1 through 4). As illustrated, the first snap-fit structure includes first and second extending portions 137, 139. In other embodiments, though, the first snap-fit structure may include greater than, fewer than, or exactly two extending portions. It is noted that the distal tip 134 may be define any structure configured to engage an anchor. A skilled artisan will be able to determine how to suitably configure the distal end to connect to an anchor according to a particular example based on various considerations, including the shape and size of the anchor and the shape and size of the main body. For example, in one embodiment the distal end may include a threaded portion for connecting to an anchor. In an alternative embodiment, the distal end may include a hook, one or more adhesives, a protrusion, or any other mechanism configured to connect to an anchor.

FIGS. 1 through 4 also illustrate the outer member 200. The outer member 200 has a main body 226 comprising a proximal end 222, a distal end 224, an outer surface 236, an inner surface 238, a lumen 228, and an endcap 250.

In the illustrated embodiment, the main body 226 is elongate and tubular and defines a third diameter $d_3$ extending directly from a first outer point 240 of the outer surface 236 to a second outer point 242 of the outer surface 236 opposite the first outer point 240 about the longitudinal axis of the main body 226. The main body 226 is substantially rectangular in cross-sectional shape and is uniform in diameter from the proximal end 222 to the distal end 224. It is noted, though, that the main body may have other cross-sectional shapes in alternative embodiments, including rectangular, elliptical, and substantially elliptical. A skilled artisan will be to determine a suitable diameter and cross-sectional shape for the main body according to a particular example based on various considerations, including the shape and size of the main body of the inner member and the shape and size of the actuator. In various embodiments, the main body may define a non-uniform diameter. For example, in one particular embodiment the main body may define a first diameter at the proximal end and a second, smaller diameter at the distal end, thus providing the main body with a distal taper.

The main body 226 defines an endcap 250 on the proximal end 222 in the illustrated embodiment. As best illustrated in FIG. 2, the endcap 250 is substantially donut-shaped and defines a passageway 252 extending from the inner surface 254 of the endcap 250 to the outer surface 256 of the endcap 250. Furthermore, the passageway 252 has a fourth diameter $d_4$ extending directly from a first outer point 262 of the outer surface 256 to a second outer point 264 of the outer surface 256 opposite the first outer point 262 about the passageway 252. The fourth diameter $d_4$ is approximately half of the third diameter $d_3$ in this embodiment. In addition, the fourth diameter $d_4$ is greater than the first diameter $d_1$ of the main body 126 of the inner member 100, but is less than the second diameter $d_2$ of the actuator 110. The fourth diameter $d_4$ may have any measurement. A skilled artisan will be able to determine suitable sizes and shapes for the endcap and the passageway according to a particular example based on various considerations, including the shape and size of the inner member of the main body and the shape and size of the actuator. In an alternative embodiment, the fourth diameter may be approximately seventy-five percent as large as the third diameter; in a different embodiment, the fourth diameter may be approximately twenty-five percent as large as the third diameter.

The endcap 250 is welded to the proximal end 222 of the main body 226 in the illustrated embodiment. It is noted, though, that the endcap 250 may be attached to the proximal end 222 in any manner. A skilled artisan will be able to determine how to connect the endcap with the proximal end according to a particular example based on various considerations, including the shape and size of the inner member of the main body and the shape and size of the actuator. In a different embodiment, the endcap may be adhesively attached, connected via one or more hooks, or threaded with the proximal end. Alternatively, the endcap may be integrally formed with the proximal end. Other embodiments exist in which the proximal end is not in contact with an endcap.

The distal end 224 defines a second snap-fit structure 232 extending proximally from a distal tip 234 defined by the distal end 224. The second snap-fit structure 232 is configured to cooperatively mate with a head member (not illustrated in the Figures). As illustrated, the second snap-fit structure 232 includes first and second extending portions 237, 239. It is noted, though, that any structure configured to engage a head member may be used. A skilled artisan will be able to determine how to suitably configure the distal end to connect to a head member according to a particular example based on various considerations, including the shape and size of the head member and the shape and size of the main body. In other embodiments, though, the second snap-fit structure may include greater than, fewer than, or exactly two extending portions. In different embodiments, the distal end may not include a second snap-fit structure; instead, the distal end may define any mechanism for connecting to a head member. For example, in one embodiment the distal end may include a threaded portion for connecting to a head member. In an alternative embodiment, the distal end may include a hook, one or more adhesives, a protrusion, or any other mechanism configured to connect to head member.

In use, and described in greater detail below, the inner member 100 is movably disposed within the outer member 200. The inner member 100 is also captive within the outer member 200. FIG. 3 illustrates the anchor assembly tool 10 in a first configuration. In the first configuration, the actuator 110 contacts the proximal end 222 of the main body 226 of the outer member 200. Additionally, the proximal end 122 of the main body 126 of the inner member 100 is disposed through the passageway 252 defined by the endcap 250 of the proximal end 222 of the main body 226 of the outer member 200. The spring 130 is disposed within the lumen 228 of the main body 228 of the outer member 200 and contacts the inner surface 254 of the endcap 250; the spring 130 is not compressed. When the anchor assembly tool 10 is in the first configuration, a first distance Al is defined that extends from the distal tip 134 of the main body 126 of the inner member 100 to the distal tip 234 of the main body 234 of the outer member 200. In an alternative embodiment, the actuator may not contact the proximal end of the outer member. In a different embodiment, the spring may be disposed within the lumen of the main body of the outer member such that the spring is adjacent, but does not contact, the inner surface of the endcap when the anchor assembly tool is in the first configuration. The spring may also be placed such that it is not adjacent the inner surface.

As indicated by arrow ZZ, the anchor assembly tool 10 is transitioned from the first configuration to the second configuration through the activation of the actuator 110 of the inner member 100. Activation of the actuator 110 occurs when a proximally-directed force is directed on the actuator 110. Upon such a proximally-directed force, the inner member 100 is advanced proximally within the outer member 200. As this occurs, the spring 130 compresses and is pressed against the inner surface 254 of the endcap 250; concurrently, the distal tip 134 of the main body 126 of the inner member 100 moves in the proximal direction toward the distal tip 234 of the main body 226 of the outer member 200. Proximally-directed force may be directed on the actuator 110 in a number of ways. In the illustrated embodiment, a user of the anchor assembly tool 10 to use his or her fingers to manually enact proximally-directed force on the actuator 110. A machine may also provide the proximally-directed force.

As illustrated in FIG. 4, the actuator 110 does not contact the proximal end 222 of the main body 226 of the outer member 200 when the anchor assembly tool 10 is in the second configuration. Additionally, the proximal end 122 of the main body 126 of the inner member 100 is disposed through the passageway defined by the endcap 250 of the proximal end 222 of the main body 226 of the outer member 200. The spring 130 is disposed within the lumen 228 of the main body 226 of the outer member 200 and continues to contact the inner surface 254 of the endcap 250; the spring 130 is compressed, however. When the anchor assembly tool 10 is in the second configuration, a second distance $\Delta_2$ is defined that extends from the distal tip 134 of the main body 126 of the inner member 100 to the distal tip 234 of the main body 234 of the outer member 200. In the illustrated embodiment, the second distance $\Delta_2$ is less than the first distance $\Delta_1$. The difference between the first and second distances $\Delta_1$, $\Delta_2$ is predetermined based on the characteristics of the inner and outer members 100, 200. Any difference between the first and second distances may be suitable. A skilled artisan will be able to determine suitable first and second distances according to a particular example based on various considerations, including the shape and size of the inner member and the shape and size of the outer member. In another embodiment, the second distance may about fifty percent as great as the first distance. In one embodiment, the second distance may be about twenty-five percent as great as the first distance. In a different embodiment, the second distance may about ten percent as great as the first distance.

Figure 5:
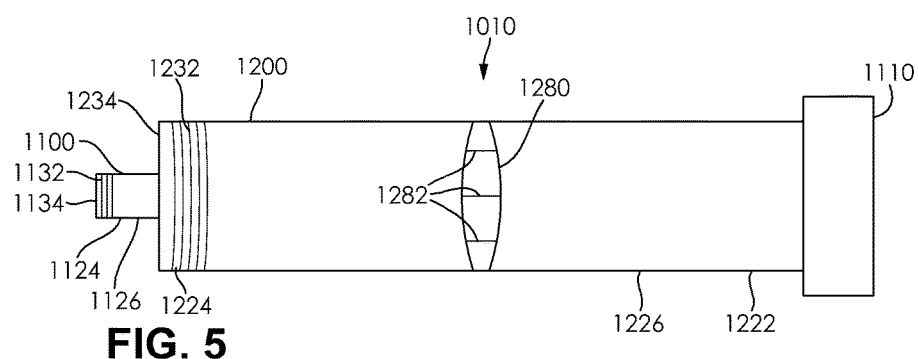
FIG. 5 is a side view of another example anchor assembly tool. The anchor assembly tool is illustrated in a first configuration.
Figure 6:
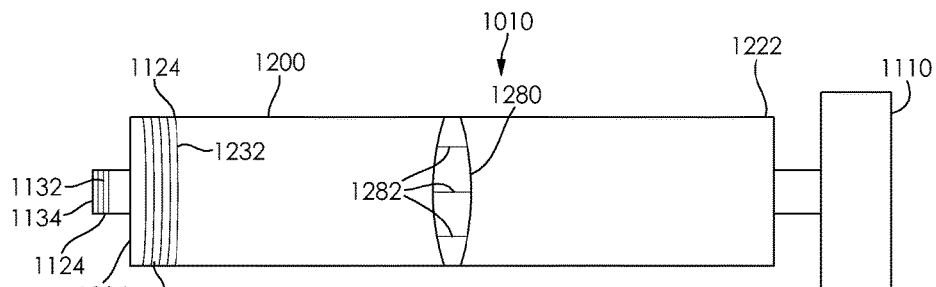
FIG. 6 is a side view of the anchor assembly tool illustrated in FIG. 5. The anchor assembly tool is illustrated in a second configuration.

Each of FIGS. 5 and 6 illustrates another anchor assembly tool 1010 or one or more components thereof. The illustrated anchor assembly tool 1010 is similar to the anchor assembly tool 10 illustrated in FIGS. 1, 2, 3, and 4 and described above, except as described below. Thus, the anchor assembly tool 1010 comprises an inner member 1100 movably disposed within an outer member 1200. The inner member 1100 comprises an actuator 1110 and a main body 1126 having a proximal end 1122, a distal end 1124, and a distal tip 1134. The outer member 1200 comprises a main body 1226 having a proximal end 1222, a distal end 1224, and a distal tip 1234.

In this embodiment, the distal end 1124 of the inner member 1100 defines a first threaded portion 1132 extending proximally from the distal tip 1134. The first threaded portion 1132 is configured to cooperatively mate with an anchor (not illustrated in FIG. 5 or 6). Any mechanism for engaging an anchor with the distal end may be used, however. A skilled artisan will be able to determine how to suitably configure the distal end to engage with an anchor according to a particular example based on various considerations, including the shape and size of the anchor and the shape and size of the main body. In a different embodiment, the distal end may not include a threaded portion; instead, the distal end may define any structure for connecting to an anchor. For example, in one embodiment the distal end may include a snap-fit structure for connecting to an anchor. In an alternative embodiment, the distal end may include a hook, one or more adhesives, a protrusion, or any other mechanism configured to connect to an anchor. Additionally, other embodiments exist in which the first threaded portion is not defined by the distal tip; rather, the first threaded portion is disposed proximal to the distal tip.

In addition, the distal end 1224 of the outer member 1200 defines a second threaded portion 1232 extending proximally from a distal tip 1234 defined by the distal end 1224. The second threaded portion 1232 is configured to cooperatively mate with a head member (not illustrated in FIG. 5 or 6). In a different embodiment, the distal end may not include a second threaded portion; instead, the distal end may define any mechanism for connecting to a head member. A skilled artisan will be able to determine how to suitably configure the distal end to connect to a head member according to a particular example based on various considerations, including the shape and size of the head member and the shape and size of the main body. For example, in one embodiment the distal end may include a snap-fit structure for connecting to a head member. In an alternative embodiment, the distal end may include a hook, one or more adhesives, a protrusion, or any other mechanism configured to connect to head member.

In this embodiment, the inner member 1100 and the outer member 1200 are attached such that they are each independently rotatable. The actuator 1110 is rotatable within the inner member 1100. The actuator 1110 is rotatable when the anchor assembly tool 1010 is in the first configuration and when the anchor assembly tool 1010 is in the second configuration. Rotation of the actuator 1110 rotates the main body 1126 of the inner member 1110, including the distal end 1124 having the first threaded portion 1132. Rotation of the actuator 1110 that, in turn, rotates the distal end 1124 enables the distal end 1124 to engage an anchor (not illustrated in FIG. 5 or 6) designed to mate with the distal end 1124 without manually inserting the anchor onto the distal end 1124 of the main body 1126.

FIGS. 5 and 6 also illustrate an outer member 1200 that is rotatable. This embodiment includes a collar 1280 defined by the main body 1226. The collar 1280 defines gripping ridges 1282. Applying rotational force to the collar 1280 or any other portion of the main body 1226 may rotate the outer member 1200. The outer member 1226 is rotatable when the anchor assembly tool 1010 is in the first configuration and when the anchor assembly tool 1010 is in the second configuration. Rotation of the outer member 1200 rotates the main body 1226 of the outer member 1200, including the distal end 1224 having the second threaded portion 1232. Rotational force applied to the collar 1280, for example, that rotates the distal end 1224 enables the distal end 1224 to engage a head member (not illustrated in FIG. 5 or 6) designed to mate with the distal end 1224 without manually inserting the head member onto the distal end 1224 of the main body 1226.

In use, the outer member 1200 will be substantially fixed in place while the actuator 1100 is rotated; a user of the anchor assembly tool 1010 may hold the outer member 1200 in place with one hand as he or she rotates the actuator 1100 with his or her other hand, for example. Furthermore, the inner member 1100 will be substantially fixed in place while the outer member 1200 is rotated, whether via rotational force on the collar 1280 or rotational force on any other portion of the main body 1226. Once each of the anchor and heat member are attached to the outer and inner members 1100, 1200, respectively, a user can apply a proximally-directed force to the actuator 1110 to move the anchor into the head member. However, other methods of advancing the anchor into the head member may be used. A skilled artisan will be able to determine how to use the anchor assembly tool according to a particular example based on various considerations, including the sizes and shapes of the inner and outer members. However, in other embodiments the outer member may not be fixed in place as the actuator is rotated. Alternatively, the inner member may not be fixed in place while the outer member is rotated in another embodiment. Other embodiments exist in which neither the inner member nor the outer member is fixed in place while the other member rotates.

Each of FIGS. 7, 8, 9, and 10 illustrates another anchor assembly tool 2010 or one or more components thereof. The illustrated anchor assembly tool 2010 is similar to the anchor assembly tool 10 illustrated in FIGS. 5 and 6 and described above, except as described below. Thus, the anchor assembly tool 2010 comprises an inner member 2100 movably disposed within an outer member 2200 and a handle 2700.

The inner member comprises 2100 an actuator 2110 and a main body 2126 having a proximal end 2122, a distal end 2124, and a distal tip 2134.

In this embodiment, the actuator 2110 has a proximal end 2112 and a distal end 2114. The actuator 2110 also defines a channel 2118; the channel 2118 defines threading 2119. The channel 2118 extends from the proximal end 2112 to the distal end 2114 of the actuator 2110 and is configured to engage a screw 2900 via the threading 2119. The distal end 2114 is disposed through a passageway 2196 of a ring member 2190. The actuator 2110 is adjacent a ring member 2190 having a proximal end 2192 and a distal end 2194 and a passageway 2196 extending from the proximal end 2192 to the distal end 2194 of the ring member 2190 which is configured to allow the distal end 2114 of the actuator 2110 to be disposed through the passageway 2196. In this embodiment, the ring member 2190 and actuator 2110 abut. In other embodiments, the ring member may not be included or the actuator may not abut it.

The inner member 2100 also comprises a housing 2188 extending away from the main body 2126. The housing 2188 includes a housing passageway 2186 extending from a first housing side 2187 to a second housing side (not illustrated in the Figures) substantially opposite the first housing side 2187. The housing 2188 is configured to engage a connecting device, such as a screw. The housing 2188 is integrally formed with the inner member 2100 in the illustrated embodiment. The housing may be attached to the inner member in any manner, however. A skilled artisan will be able to determine how to configure the housing with regard to the inner member according to a particular example based on various considerations, including the sizes and shapes of the inner and outer members. In other embodiments, the housing may be attached to the inner member via welding, suturing, an adhesive, or any other suitable technique.

In this embodiment, the outer member 2200 comprises a first piece 2210, a second piece 2450, and a rotatable collar 2300. The first piece 2210 has a proximal end 2212, a distal end 2214, a main body 2216 extending from the proximal end 2212 to the distal end 2214, a lumen 2218 extending from the proximal end 2212 to the distal end 2214, an outer surface 2236, and an inner surface 2238.

The second piece 2450 has a proximal end 2452, a distal end 2454, a main body 2456 extending from the proximal end 2452 to the distal end 2454, a lumen 2458 extending from the proximal end 2452 to the distal end 2454, an outer surface 2466, an inner surface 2468, a window 2490, and an extension 2494. The proximal end 2452 of the second piece 2450 defines a channel (not illustrated in the FIGURES) extending distally from the proximal end 2452.

The rotatable collar 2300 is disposed between the first piece 2210 and the second piece 2450 has a disc-shaped portion 2310 disposed between an upper portion 2380 and a tapered portion 2350. The disc-shaped portion 2310 has an upper surface 2312, a middle surface 2314, outer surface 2336, and an inner surface 2338. The upper portion 2380 has a main body 2382 and defines a groove 2384 extending along the surface 2386 of the main body 2382 of the upper portion 2380. The tapered portion 2350 has a proximal end 2352 and a distal end 2354. The rotatable collar 2300 defines a lumen 2318 extending from the upper surface 2312 of the disc-shaped portion 2310 to the distal end 2354 of the tapered portion 2350. The distal end 2454 of the second piece 2450 is attached to the upper surface 2312 of the disc-shaped portion 2310 of the rotatable collar 2300. The first piece 2210 is integrally formed with the rotatable collar 2300; the distal end 2354 of the tapered portion 2350 of the rotatable collar 2300 contacts the proximal end 2212 of the first piece 2210. Each of the lumens 2218, 2458, 2318 is aligned to form a continuous lumen (not illustrated in the Figures) extending from the distal end 2214 of the first piece 2210 to the proximal end 2452 of the second piece 2450.

The main body 2216 of the first piece 2210 is elongate and tubular and defines rows of fenestrations 2244 extending from the inner surface 2238 to the outer surface 2236 of the first piece 2210. The first row has four fenestrations 2244 and is substantially opposite the second row, which also has four fenestrations 2244. In the illustrated embodiment, each fenestration 2244 is rounded rectangular in shape. It is noted, though, that any number of fenestrations having any shape may be arranged in rows or any other formation. A skilled artisan will be able to determine a suitable number of fenestrations and their shapes and alignments according to a particular example based on various considerations, including the shape and size of the outer member and the shape and size of the inner member. In an alternative embodiment, each fenestration may be circular. In other embodiments, each fenestration may be circular, elliptical, triangular, rectangular, or any other shape. Furthermore, in other embodiments the main body may define zero, one, two, three, five, or more than five total fenestrations and the fenestrations may be grouped into zero, one, three, or more than three rows.

The first piece 2210 also defines a fifth diameter $d_5$ extending directly from a first outer point 2250 of the outer surface 2236 to a second outer point 2252 of the outer surface 2236 opposite the first outer point 2250 about the longitudinal axis of the first piece 2210. The first piece may define any suitable fifth diameter.

The distal end 2214 of the first piece 2210 defines a second threaded portion 2232 extending proximally from a distal tip 2234 defined by the distal end 2214. The second threaded portion 2232 is configured to cooperatively mate with a head member (not illustrated in the FIGURES). In a different embodiment, the distal end may not include a second threaded portion; instead, the distal end may define any mechanism for connecting to a head member. A skilled artisan will be able to determine how to suitably configure the distal end to engage a head member according to a particular example based on various considerations, including the shape and size of the head member and the shape and size of the inner member. For example, in one embodiment the distal end may include a snap-fit structure for connecting to a head member. In an alternative embodiment, the distal end may include a hook, one or more adhesives, a protrusion, or any other mechanism configured to connect to head member.

As discussed above, the first piece 2210 is integrally formed with the rotatable collar 2300 such that rotation of the rotatable collar 2300 rotates the first piece 2210. The distal end 2354 of the tapered portion 2350 contacts the proximal end 2212 of the first piece 2210 in the illustrated embodiment. The first piece and rotatable collar may be attached in any way, however. A skilled artisan will be able to determine whether to integrally form the first piece with the rotatable collar and, if not, how to attach the first piece and rotatable collar according to a particular example based on various considerations, including the shape and size of the outer member and the shape and size of the inner member. In an alternative embodiment, the first piece may not be integrally formed with the rotatable collar and, instead, may be welded to the rotatable collar. In other embodiments, the first piece may be attached to the rotatable collar through the use of one or more adhesives, by a system of hooks, or by a snap-fit structure.

Figure 9:
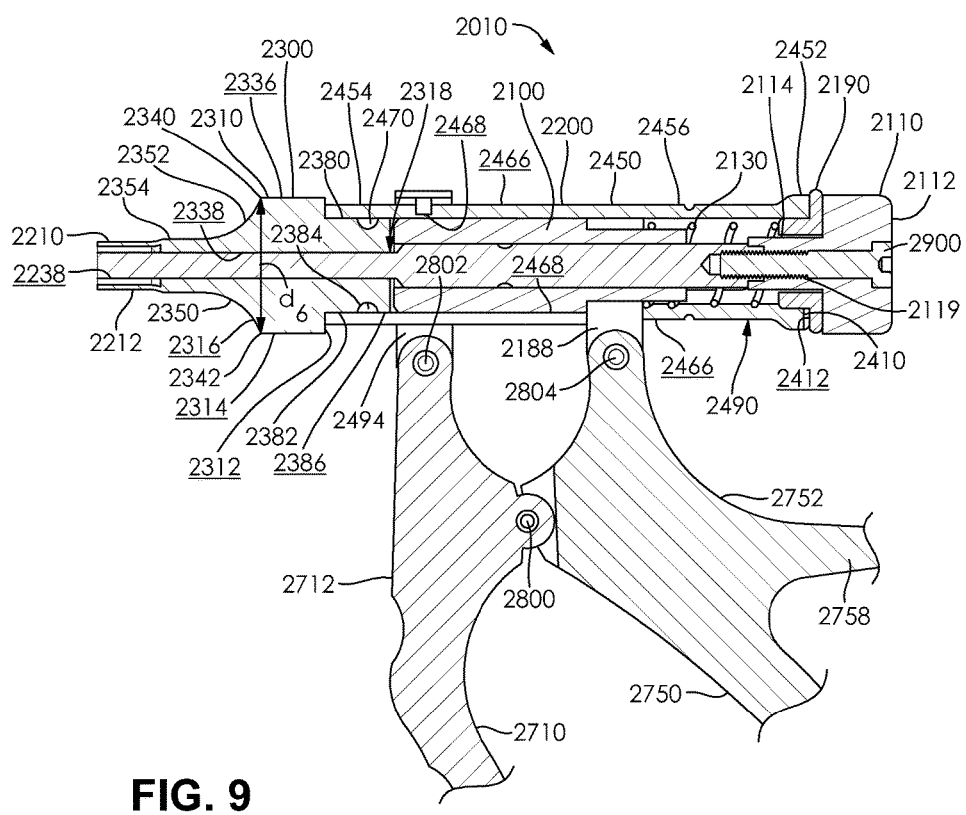
FIG. 9 is a magnified cross-sectional view of Area I of the anchor assembly tool illustrated in FIG. 8 taken along its lengthwise axis.

As best illustrated in FIG. 9, the upper portion 2380 of the rotatable collar 2300 defines a groove 2384 extending along the surface 2386 of the main body 2382. As discussed below, the groove 2384 is configured to cooperatively mate with a portion of the second piece 2450 to facilitate rotational movement of the rotatable collar 2300 and the first piece 2210 while still maintaining a connection with the second piece 2450. The groove 2384 is substantially semi-circular in cross-sectional shape, though the groove may have any suitable cross-sectional shape. A skilled artisan will be able to determine a suitable shape and size of the groove according to a particular example based on various considerations, including the shape and size of the outer member and the shape and size of the inner member. In other embodiments, the groove may be square, rectangular, elliptical, ovoid, or any other cross-sectional shape.

In the illustrated embodiment, the disc-shaped portion 2310 defines a plurality of ridges 2382 along the outer surface 2336. The plurality of ridges 2382 is included to assist in the gripping of the rotatable collar 2300. Any structure may be included to assist in gripping, however. A skilled artisan will be able to determine whether a structure designed to assist in gripping the outer member is desirable and what particular structure to use according to a particular example based on various considerations, including the shape and size of the outer member and the shape and size of the inner member. In alternative embodiments, the rotatable collar may not have ridges; it may also comprise grooves, protrusions, a single ridge, or any other structure to assist in gripping the rotatable collar.

The disc-shaped portion 2310 also defines a sixth diameter $d_6$ extending directly from a first outer point 2340 of the upper surface 2312 to a second outer point 2342 of the upper surface 2312 opposite the first outer point 2340. The disc-shaped portion may define any suitable sixth diameter.

The second member 2200 also includes a tapered portion 2350 of the rotatable collar 2300. The distal end 2354 of the tapered portion 2350 has the same diameter as the first piece 2210 and the proximal end 2352 of the tapered portion 2350 has the same diameter as the disc-shaped portion 2310. Thus, the tapered portion 2350 tapers in the distal direction.

The main body 2456 of the second piece 2450 is elongate and tubular and defines a protrusion 2470 disposed on the inner surface 2468 of the distal end 2454. The protrusion 2470 forms a ring about the longitudinal axis of the main body 2456. In addition, the protrusion 2470 is substantially semi-circular in cross-sectional shape. The protrusion 2470 is adapted to mate with the groove 2384 to facilitate rotational movement of the rotatable collar 2300 and first piece 2210 about the longitudinal axis of the rotatable collar 2300 while still maintaining a connection between the second piece 2450 and the rotatable collar 2300. It is noted, however, that any suitable structure for maintaining such a connection while still allowing the collar to rotate may be used. A skilled artisan will be able to determine a suitable protrusion configuration according to a particular example based on various considerations, including the shape and size of the outer member and the shape and size of the inner member. In other embodiments, however, the protrusion may have any cross-sectional shape, including circular, triangular, and rounded rectangular. In different embodiments, main body may define a groove while the rotatable collar may define a protrusion.

The proximal end 2452 of the second piece 2450 defines an endcap 2410 that is similar to the endcap 250 illustrated in FIG. 2, for example, and discussed above.

FIG. 9 best illustrates a window 2490 defined by the main body 2456 of the second piece 2450. The window 2490 extends from the outer surface 2466 to the inner surface 2468 of the second piece 2450. In the illustrated embodiment, the window 2490 is substantially rectangular in shape and is disposed on the main body 2456 adjacent the endcap 2410. In other embodiments, the window may have any shape, including circular, triangular, square, and any other shape. A skilled artisan will be able to determine whether to include a window and, if so, a suitable shape of and placement for the window according to a particular example based on various considerations, including the shape and size of the outer member and the shape and size of the inner member. In various embodiments, the window may be disposed anywhere on the main body of the second piece. In a different embodiment, the main body does not include a window; in another embodiment, the main body includes two or more windows.

The illustrated embodiment also includes a first extension 2494 attached to the outer surface 2466 of the main body 2456 of the second piece 2450; the extension 2494 has a first side 2495 and a second side (not illustrated in the Figures). The extension 2494 is c-shaped, protrudes from the outer surface 2466, and defines a channel 2498 extending from the first side 2495 to the second side. As best illustrated in FIG. 9, the channel 2498 is circular in shape; the channel 2498 is also configured to mate with a screw, such as screw 2802.

The illustrated embodiment also illustrates a handle 2700 comprising first and second handle portions 2710, 2750. The first handle portion 2710 includes a proximal end 2712, a distal end 2714, a main body 2716 extending from the proximal end 2712 to the distal end 2714, a first surface 2730, and a second surface (not illustrated in the FIGURES) substantially opposite the first surface 2730. Furthermore, the proximal end 2712 defines a first passageway 2720 extending from the first surface 2730 to the second surface configured to house a screw or other structure suitable for connecting the first handle portion 2710 to the second piece 2450. The main body 2716 also defines a first center passageway 2722 extending from the first surface 2730 to the second surface that is suitable to house a screw or other structure suitable for connecting the first handle portion 2710 to the second handle portion 2750. Optionally, the first handle portion 2710 may define handle ridges 2740 beginning at the distal end 2714 and extending toward the proximal end 2712. The handle ridges 2740 enable a user to easily grasp the first handle portion 2710.

The second handle portion 2750 includes a proximal end 2752, a distal end 2754, a main body 2756 extending from the proximal end 2752 to the distal end 2754, a first surface 2760, a second surface (not illustrated in the Figures) substantially opposite the first surface 2760, and an extended portion 2758. The proximal end 2752 defines a second passageway 2770 extending from the first surface 2760 to the second surface; the second passageway 2770 is configured to house a screw or other structure suitable for connecting the second handle portion 2750 to the inner member 2100, and is circular in shape. The main body 2756 also defines a second center passageway 2772 extending from the first surface 2760 to the second surface that is suitable to house a screw or other structure suitable for connecting the first handle portion 2710 to the second handle portion 2750. The second handle portion 2750 may have any shape and size. The extended portion 2758 extends from the main body 2756 in the proximal direction, away from the first piece 2210. In alternative embodiments, the extended portion may not be included.

The first handle portion 2710 and the second handle portion 2750 are connected via a first screw 2800 that is inserted through the first and second center passageways 2722, 2772, after the first and second center passageways 2722, 2772 have been aligned. The first and second handle portions may be connected in any suitable manner, however. A skilled artisan will be able to determine how to connect the first and second handle portions according to a particular example based on various considerations, including the shape and size of the outer member and the shape and size of the inner member. In another embodiment, the first and second handle portions are connected via a different mechanical device, such as a pin member. In another embodiment, the first and second portions are integrally formed.

The respective proximal ends 2712, 2752 of the first and second handle portions 2710, 2750 are attached to the main bodies 2456, 2126 of the respective second piece 2450 of the outer member 2200 and the inner member 2100. A second screw 2802 is inserted through the first passageway 2720 and the channel 2498 of the extension 2494, when the first passageway 2720 and channel 2498 are aligned, to connect the first handle portion 2710 to the second piece 2450. A third screw 2804 is inserted through the housing passageway 2186 and the second passageway 2770, when the housing passageway 2186 and the second passageway 2770 are aligned, to connect the main body 2126 of the inner member 2100 to the second handle portion 2750. The second handle portion 2750 is connected to the main body 2126 of the inner member 2100 through the a window 2490 defined by the main body 2456 of the second piece 2450. The first and second handle portions may be attached to the outer member and inner member in any suitable manner, however. A skilled artisan will be able to determine how to connect the handle portions to the anchor assembly tool according to a particular example based on various considerations, including the shape and size of the outer member and the shape and size of the inner member. In an alternative embodiment, the handle portions may be connected to their respective main bodies through other means, such as welding or the use of at least one adhesive. In a different embodiment, one or both of the handle portions may be integrally formed with the main bodies to which they respectively connect.

Figure 8:
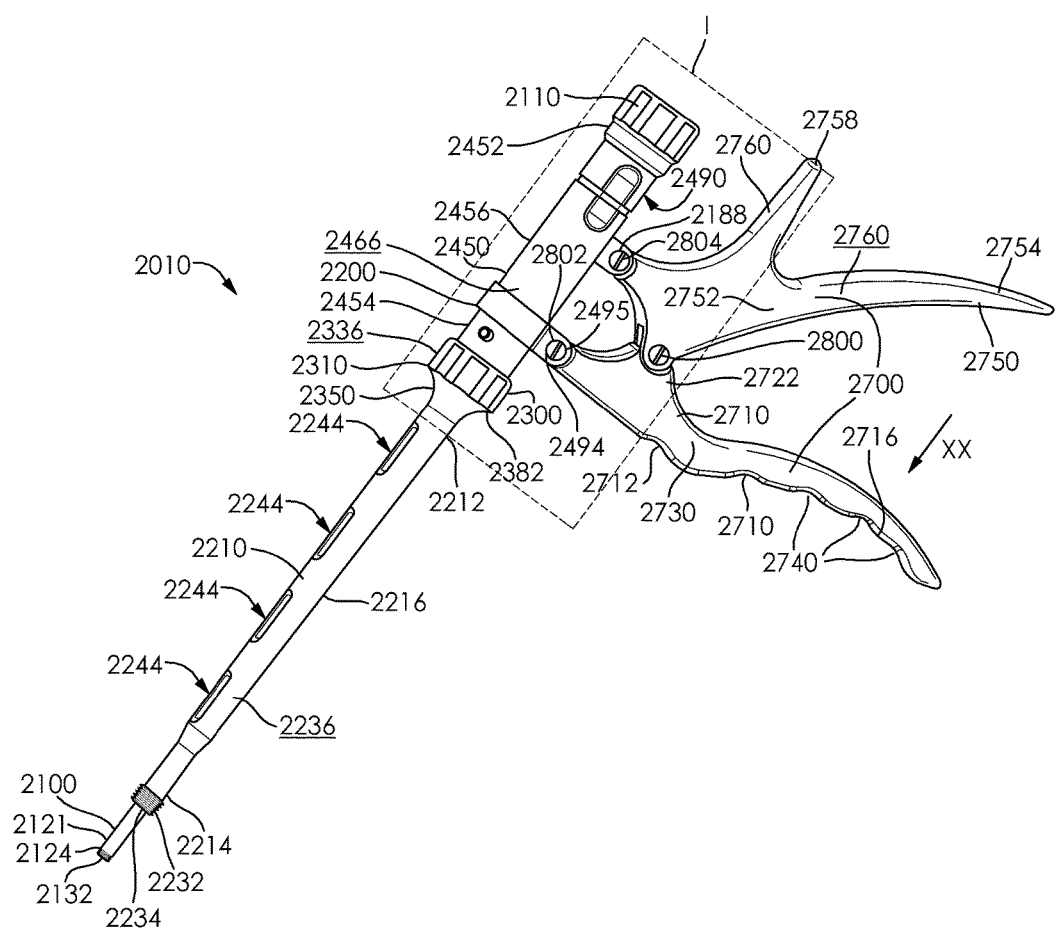
FIG. 8 is a perspective view of the anchor assembly tool illustrated in FIG. 7. The anchor assembly tool is illustrated in a first configuration.
Figure 10:
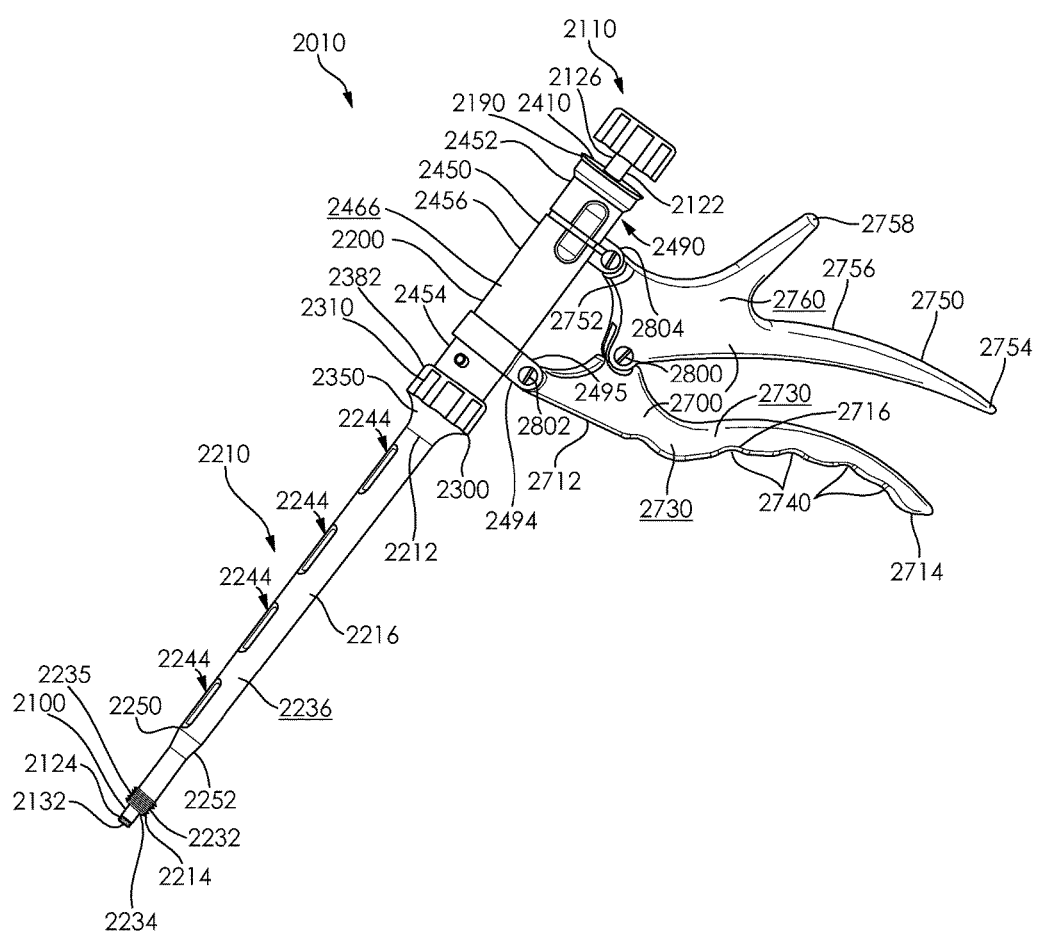
FIG. 10 is a perspective view of the anchor assembly tool illustrated in FIG. 8. The anchor assembly tool is illustrated in a second configuration.

In use, and described in greater detail below, the inner member 2100 is movably disposed within the outer member 2200. FIG. 8 illustrates the anchor assembly tool 2010 in a first configuration. FIG. 10 illustrates the anchor assembly tool 2010 in a second configuration. In the first configuration, the actuator 2110 is adjacent the proximal end 2452 of the second piece 2450 of the outer member 2200. Additionally, the proximal end 2122 of the main body 2126 of the inner member 2100 is disposed through the passageway 2414 defined by the endcap 2410 of the second piece 2452. The spring 2130 is disposed within the lumen 2458 of the second piece 2450 and is adjacent the inner surface 2412 of the endcap 2410. When the anchor assembly tool 2010 is in the first configuration, the spring 2130 is not compressed. The spring 2130 is visible through the window 2490 defined by the main body 2456 of the second piece 2450.

As indicated by arrow XX, the anchor assembly tool 2010 is transitioned from the first configuration to the second configuration through the activation of the handle 2700. Activation of the handle 2700 occurs when a distally-directed force is directed on the second handle portion 2750. As this occurs, the spring 2130 compresses and is pressed against the inner surface 2412 of the endcap 2410. The distal end 2124 of the inner member 2100 moves toward the distal end 2214 of the first piece 2210 of the outer member 2200. Upon such a force, the inner member 2100 is advanced proximally relative to the outer member 2200. Typically, a human hand will provide the distally-directed force on the second handle portion 2750. This can occur once the anchor (described below) has engaged a bone (not illustrated in the FIGURES) In other embodiments, a machine may provide the distally-directed force.

The actuator 2110 is not adjacent the proximal end 2452 of the second piece 2450 of the outer member 2200 when the anchor assembly tool 2010 is in the second configuration. Additionally, the proximal end 2122 of the main body 2126 of the inner member 2100 is at least partially disposed through the passageway 2414 defined by the endcap 2410 of the second piece 2452. The spring 2130 is disposed within the lumen 2458 of the second piece 2450 and is in contact with the inner surface 2412 of the endcap 2410. When the anchor assembly tool 2010 is in the second configuration, however, the spring 2130 is compressed.

The anchor assembly tool 2010 defines a predetermined distance that the distal end 2214 of the first piece 2210 of the outer member 2200 moves relative to the distal end 2124 of the inner member 2100 upon activation of the handle 2700. When the anchor assembly tool 2010 is in the first configuration, the distal end 2124 is disposed such that none of the first threaded portion 2132 is disposed within the lumen 2218 of the first piece 2210 of the outer member 2200. When the anchor assembly tool 2010 is in the second configuration, the distal end 2124 continues to be disposed such that none of the threaded portion 2132 is disposed within the lumen 2218 of the first piece 2210 of the outer member 2200. However, an adjacent portion 2121, which abuts the distal end 2124 having the first threaded portion 2132, is disposed within the lumen 2218 of the first piece 2210 of the outer member 2200 when the device is in the second configuration. The difference between the positioning of the distal end 2124 relative to the distal end 2214 of the first piece 2210 of the outer member 2200 in the first and second configurations determines the predetermined distance. Any suitable predetermined distance that the distal end of the inner member moves may be utilized in various embodiments. A skilled artisan will be able to determine a suitable predetermined distance of the inner member according to a particular example based on various considerations, including the shape and size of the outer member and the shape and size of the inner member. In another embodiment, the entire threaded portion of the distal end may be disposed within the lumen of the first piece when the anchor assembly tool is in the second configuration. In a different embodiment, the adjacent portion may be disposed outside of the lumen of the first piece of the outer member when the anchor assembly tool is in the second configuration. Other suitable distances may be greater than or less than that which is illustrated and has been described.

Each of FIGS. 11A, 11B, 12A, and 12B illustrates the anchor assembly tool 2010 and an associated head member 3800 and anchor 3900.

The head member 3800 is engaged with the distal end 2214 of the first piece 2210 of the outer member 2200. The head member 3800 includes a proximal end 3802 defining a proximal opening 3832, a distal end 3804 defining a distal opening 3834, a main body 3806 extending from the proximal end 3802 to the distal end 3804, a lumen 3810 extending from the proximal end 3802 to the distal end 3804, an inner surface 3812 defining a head member threaded portion 3814, a c-shaped ring 3850, and a compression spring 3852 disposed on the inner surface 3812. The head member 3800 also defines a first width $w_1$ extending from a first point 3820 disposed on the inner surface 3812 of the lumen 3810 to a second point 3822 disposed on the inner surface 3812 that is directly opposite the first point 3820 about the longitudinal axis of the head member 3800. The first width $w_1$ represents the smallest width of the lumen 3810, not including the head member threaded portion 3814.

The illustrated embodiment also includes an anchor 3900 engaged with the distal end 2124 of the inner member 2100. The anchor 3900 includes a shaft 3901, a head 3902, a recess 3904 defined by the head 3902, an inner surface 3906, an anchor threaded portion 3908 defined by the inner surface 3906, and a head outer surface 3910. The anchor 3900 also defines a second width $w_2$ extending from a first point 3920 disposed on the head outer surface 3910 to a second point 3922 disposed on the head outer surface 3910 that is directly opposite the first point 3920 about the longitudinal axis of the anchor 3900. The second width $w_2$ represents the largest width of any portion of the anchor 3900.

Figure 11A:
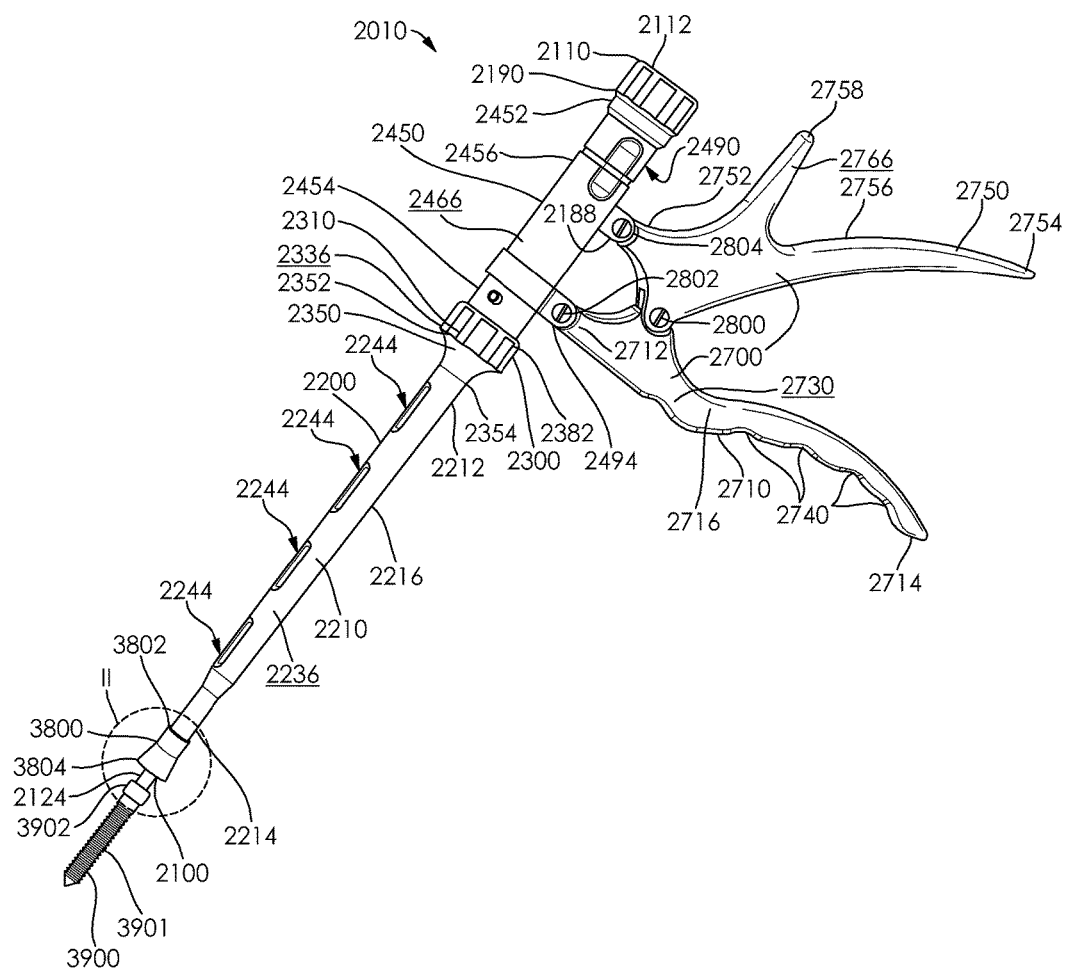
FIG. 11A is a perspective view of the anchor assembly tool illustrated in FIG. 7 with an associated anchor and head member. The anchor assembly tool is illustrated in a first configuration.
Figure 12A:
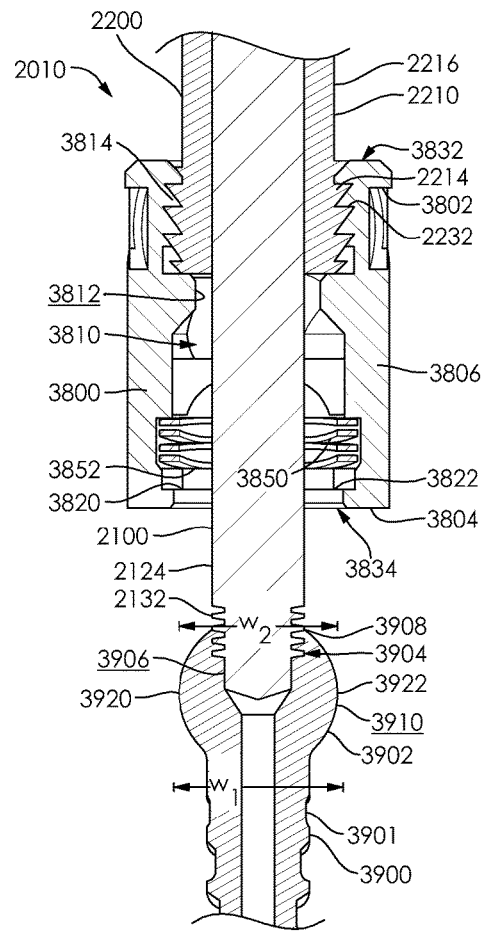
FIG. 12A is a magnified lengthwise cross-sectional view of Area II of the anchor assembly tool illustrated in FIG. 11A.

When the handle 2700 is in the first configuration the anchor head 3902 is disposed outside of the head member 3800, as illustrated in FIGS. 11A and 12A. As the handle 2700 is activated, however, the anchor 3900 is moved within the head member 3800. The first width $w_1$ of the lumen 3810 of the head member 3800 is greater than the second width $w_2$ of the head 3902 of the anchor 3900. As such, the head 3902 is slidably movable into distal opening 3834 of the distal end 3804.

Figure 11B:
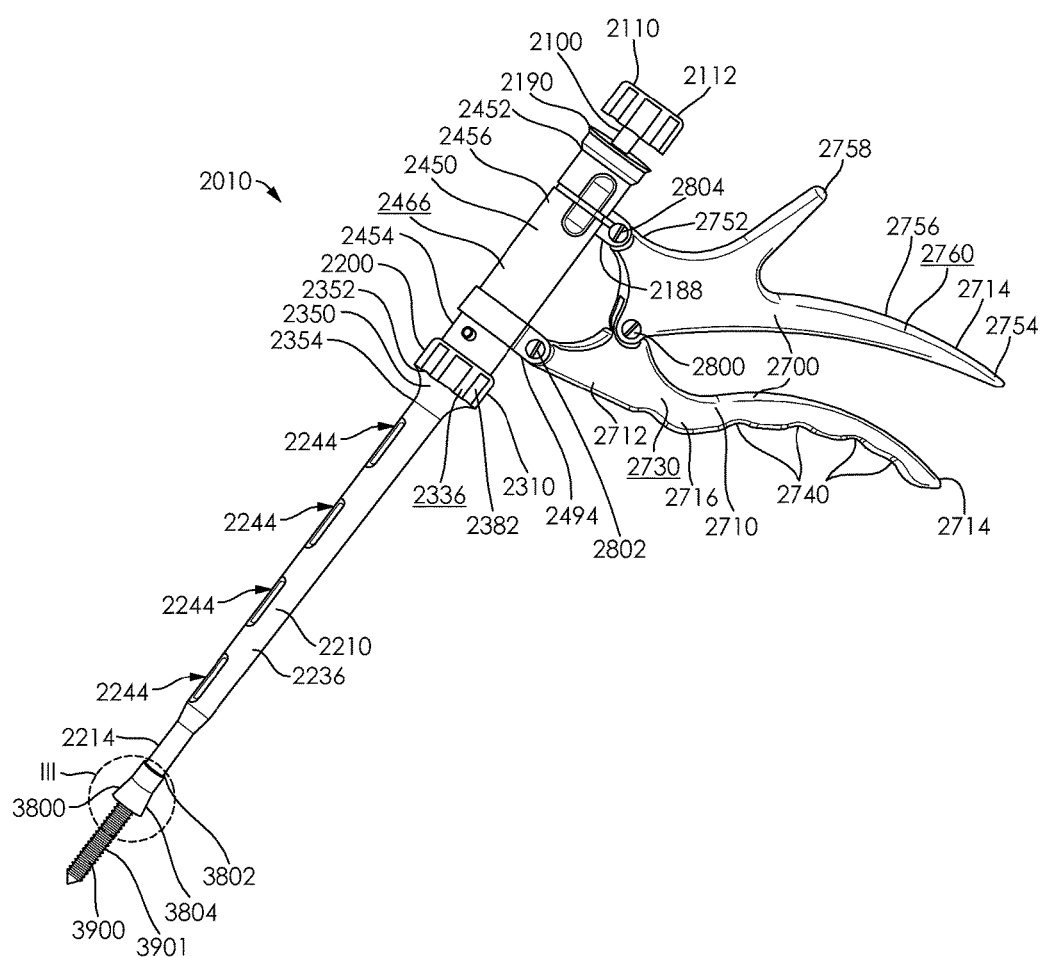
FIG. 11B is a perspective view of the anchor assembly tool, anchor, and head member illustrated in FIG. 11A. The anchor assembly tool is illustrated in a second configuration.
Figure 12B:
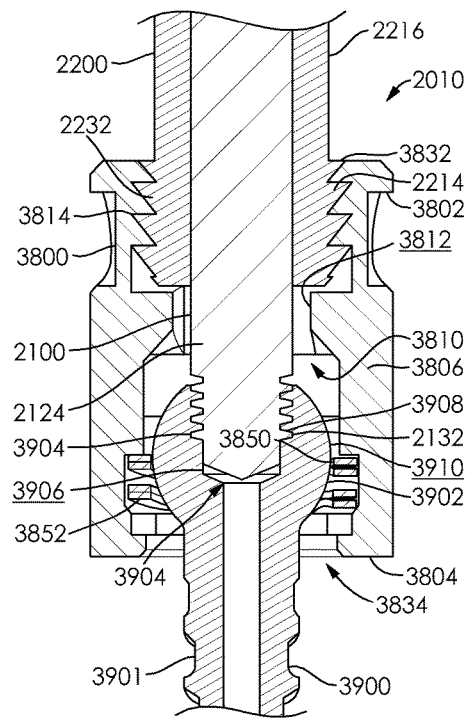
FIG. 12B is a magnified lengthwise cross-sectional view of Area III of the anchor assembly tool illustrated in FIG. 11B.

FIGS. 11B and 12B illustrate the head 3902 of the anchor 3900 disposed within the lumen 3810 of the head member 3800. Transition of the anchor assembly tool 2010 from the first configuration to the second configuration places the anchor 3900 within the head member 3800. The head 3902 is disposed within the lumen 3810 proximal to the c-shaped ring 3850. In order for the head 3902 to be disposed proximal to the c-shaped ring 3850, the outer member 2200 must be moved distally with sufficient force to radially expand the c-shaped ring 3850 enough to allow the head 3902 to pass through the c-shaped ring 3850. The coil spring of a compression spring 3852, disposed proximal to the of the c-shaped ring 3850 within the head member 3800, will be compressed as the head 3902 passes through the c-shaped ring 3850, but will return to its resting position once the head 3902 is housed within the lumen 3810. Once the head 3902 is disposed in the lumen 3810 proximal to the c-shaped ring 3850, the c-shaped ring 3850 will maintain the head 3902 within the head member 3800. It is noted that any suitable mechanism for maintaining the anchor within the head member may be used. A skilled artisan will be able to determine how to insert the anchor into the head member according to a particular example based on various considerations, including the shape and size of the anchor and the shape and size of the head member. In an alternative embodiment, a magnet may be used in place of a spring to hold the head within the head member. Alternatively, a lock can be inserted into the distal end of the head member distal to the head after the head is moved into the lumen through use of the handle.

Figure 12C:
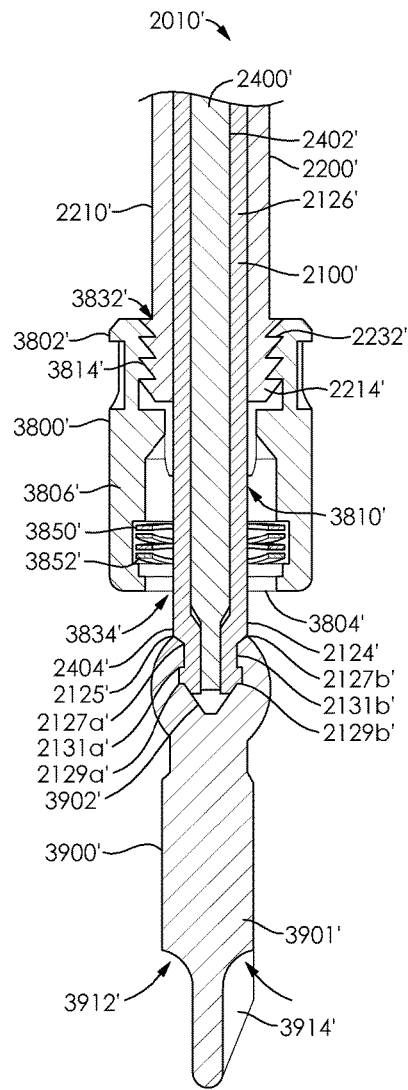
FIG. 12C is a magnified partial lengthwise cross-sectional view of an alternative anchor assembly tool, anchor, and head member. The anchor assembly tool, anchor, and head member are illustrated in a first configuration.
Figure 12D:
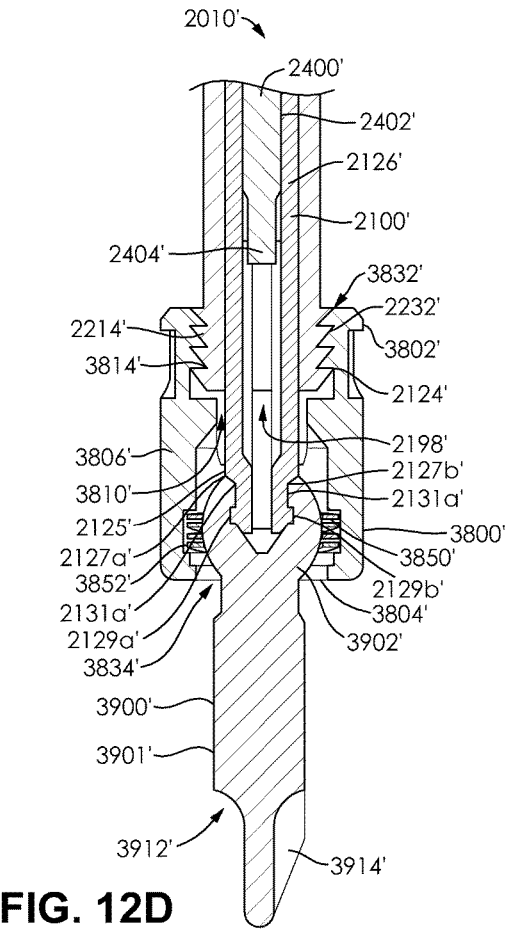
FIG. 12D is a side view of the alternative anchor assembly tool, anchor, and head member illustrated in FIG. 12C. The anchor assembly tool, anchor, and head member are illustrated in a second configuration.
Figure 12E:
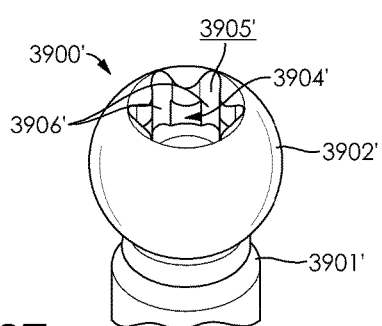
FIG. 12E is a partial perspective view of the anchor illustrated in FIG. 12C.

Each of FIGS. 12C, 12D, and 12E illustrates an alternative anchor assembly tool 2010', head member 3800', anchor 3900', or one or more components thereof. Each of the anchor assembly tool 2010', head member 3800', and anchor 3900' are similar to the anchor assembly tool 2010, head member 3800, and anchor 3900, respectively, described above, except as described below.

Thus, the anchor assembly tool 2010' includes an inner member 2100' movably disposed within an outer member 2200'. The inner member 2100' includes a main body 2126' and a distal end 2124'. The outer member 2200' includes a first piece 2210' that has a distal end 2214'. The distal end 2214' defines a second threaded portion 2232'. The head member 3800' includes a proximal end 3802' defining a proximal opening 3832', a distal end 3804' defining a distal opening 3834', a main body 3806' extending from the proximal end 3802' to the distal end 3804', a lumen 3810' extending from the proximal end 3802' to the distal end 3804', a head member threaded portion 3814', a c-shaped ring 3850', and a compression spring 3852'. The anchor 3900' includes a shaft 3901' and a head 3902'.

In the illustrated embodiment, the inner member 2100' defines a lumen 2198' that extends from the distal end 2124' (along the main body 2126') to the proximal end (not illustrated in the FIGURES) of the inner member 2100'. The distal end 2124' defines a snap-fit structure 2125' designed to engage the head 3902' of the anchor 3900'. The snap-fit structure 2125' includes a split shaft structure having a first shaft 2127a' and a second shaft 2127b' substantially opposite the first shaft 2127a' about the longitudinal axis (not illustrated in the FIGURES) of the inner member 2100'. The first shaft 2127a' defines a protuberance 2129a' at the most distal portion of the first shaft 2127a' and a recess 2131a' adjacent the protuberance 2129a'. Each of the recess 2131a' and the protuberance 2129a' has a smaller diameter than that of the inner member 2100'. The second shaft 2127b' defines a protuberance 2129b' at the most distal portion of the second shaft 2127b' and a recess 2131b' adjacent the protuberance 2129b'. Each of the recess 2131b' and the protuberance 2129b' has a smaller diameter than that of the inner member 2100'. The inner member 2100' has a compressed configuration, in which the first and second shafts 2127a', 2127b' engage the anchor head 3902' and an expanded configuration, in which the first and second shafts 2127a', 2127b' still engage the anchor head 3902', but are radially expanded relative to the longitudinal axis of the inner member 2100' as compared to their positions when in the compressed configuration. This arrangement will be described in greater detail below. In other embodiments, however, the distal end of the inner member may comprise any structure to engage the head of an anchor. A skilled artisan will be able to determine how to suitably configure the distal end of the inner member according to a particular example based on various considerations, including the size and shape of the anchor head and the size and shape of the outer member. In a different embodiment the distal end of the inner member may be threaded. In another embodiment, the distal member may include any other mechanical structure. In other embodiments, the distal end of the inner member may have a diameter that is smaller than, equal to, or about equal to the diameter of one or both of the protuberances and recesses.

An inner shaft 2400' is slidably disposed within the inner member 2100'. The inner shaft 2400' includes a main body 2402' which defines a distal end 2404'. The distal end 2404' has a smaller diameter than that of the main body 2402'. The inner shaft 2400' is slidably movable from a retracted position, in which the distal end 2404' is not adjacent the distal end 2124' and first and second shafts 2127a', 2127b', to an extended position, in which the distal end 2404' is substantially adjacent the distal end 2124' and first and second shafts 2127a', 2127b'. The inner shaft 2400' is advanced through the inner and outer members 2100', 2200' through the use of a tab (not illustrated in the FIGURES) that extends through a window (not illustrated in the Figures) that is cooperatively defined by the inner and outer members 2100', 2200'. Thus, the inner shaft 2400' is captive within the anchor assembly tool 2010'. In other embodiments, however, the inner shaft may have different characteristics and may be advanced and retracted through the anchor assembly tools via a different mechanism.

The distal end 2404' is configured to transition the inner member 2100' from its compressed configuration to its expanded configuration. More specifically, when the distal end 2404' is in its extended position, it extends into the most distal portion of the lumen 2198' of the inner member 2100' and forces the snap-fit structure 2125' to expand radially relative to the longitudinal axis of the inner member 2100'.

This, in turn, forces the first and second shafts 2127a', 2127b' to more rigidly engage the anchor head 3902' than they engage the anchor head 3902' when the distal end 2404' is not adjacent the snap-fit structure 2125'. Consequently, the inner shaft 2400' provides additional support to the anchor assembly tool 2010' when it is in the extended position by increasing the stability of the connection between the inner member 2100' and the head member 3800'. A skilled artisan will be able to suitably shape, size, and configure the inner shaft according to a particular example based on various considerations, including the size and shape of the inner member and the size and shape of the anchor head. In a different embodiment, the distal end of the inner shaft may have the same diameter as the main body of the inner shaft. In a different embodiment, the inner shaft may not be captive within the inner and outer members; rather, it may be removably inserted through openings defined at the proximal ends of the inner and outer members. In other embodiments, the inner shaft may be omitted.

As best illustrated in FIG. 12C, the anchor 3900' includes a head 3802' which defines a recess 3904' defined by an inner surface 3905'. The inner surface 3905' also defines a set of grooves 3906' which extend about the longitudinal axis (not illustrated in the FIGURES) of the anchor 3900'. The set of grooves 3906' are configured to engage the distal end 2124' (and, more specifically, the first and second shafts 2127a', 2127b') of the inner member 2100'. Furthermore, the shaft 3901' of the anchor 3900' defines a distal end 3910' which defines a cutout 3912' and a groove 3914'. The anchor may have any shape and size in other embodiments, however. A skilled artisan will be able to determine how to suitably size and shape the anchor according to a particular example based on various considerations, including the size and shape of the inner shaft and distal end of the inner member. In a different embodiment, the inner surface may define threads that are configured to mate with a threaded portion of the inner shaft or inner member. In another embodiment, the head may include a different mechanical structure configured to engage the inner member distal end. In other embodiments, the distal end of the shaft may not define one or both of the cutout and groove.

In use, and described in greater detail below, the inner member 2100' is disposed within the outer member 2200' and the inner shaft 2400' is movably disposed within the inner member 2100'. In one configuration, as illustrated in FIG. 12C, the head member 3800' engages the distal end 2214' of the first piece 2210' of the outer member 2200' via the head member threaded portion 3814'. The snap-fit structure 2125' of the inner member 2100' engages the set of grooves 3906' defined by the inner surface 3905' and the distal end 2404' of the inner shaft 2400' is disposed within the distal portion of the lumen 2198'. The inner shaft 2400' is in its extended position and, therefore, provides sufficient force to allow the inner member 2100' to rigidly engage the anchor 3900'. At this point, the handle (not illustrated in the FIGURES) is activated and the inner member 2100' is advanced into the outer member 2200' such that the anchor 3900' is disposed through the distal opening 3834' and within the lumen 3810' of the head member 3800'. This occurs while the inner shaft 2400' is within the distal portion of the lumen 2198' and adjacent the first and second shafts 2127a', 2127b'; accordingly, the inner member 2100' still rigidly engages the anchor 3900' when the anchor 3900' is moved proximally.

After activation of the handle, the head 3902' is disposed within the head member 3800' proximal to the c-shaped ring 3850', as illustrated in FIG. 12D. The inner shaft 2400' is then retracted from the head 3902' and disposed in its retracted position. The first and second shafts 2127a', 2127b' of the snap-fit structure 2125' are expanded radially relative to the longitudinal axis of the inner member 2100' upon retraction of the inner shaft 2400'. Accordingly, while the snap-fit structure 2125' still engages the anchor 3900', it does not do so as rigidly or securely as it does when the inner shaft 2400' extends into the most distal portion of the lumen 2198' of the inner member 2100'. Next, the head member 3800' is detached from the distal end 2214' of the outer member 2200'; the anchor 3900' is subsequently detached from the distal end 2124' of the inner member 2100'. The anchor assembly tool 2010' may be used in a number of other manners, however. A skilled artisan will be able to determine how to suitably configure and use the anchor assembly tool according to a particular example based on various considerations, including the size and shape of the head members and anchors. In a different embodiment, the head member may be detached from the outer member after the anchor is detached from the inner member.

Each of FIGS. 13, 14, 15, 16, and 17 illustrates a driver 3000 or one or more components thereof. The driver 3000 includes an inner member 3100, an outer member 3200, a grasping member 3300, and a cap 3400. The inner member 3100 is movably disposed within the outer member 3200. Each of FIGS. 14, 15, 16, and 17 also illustrates an associated anchor, such as the anchor 3900 illustrated in FIGS. 11A, 11B, 12A, and 12B and described above.

The inner member 3100 has a proximal end 3102, a distal end 3104, a main body 3106, an outer surface 3114, and an inner surface 3116. The inner member 3100 also defines a lumen 3108 extending from the proximal end 3102 to the distal end 3104. The lumen 3108 houses a grasping member 3300.

The main body 3106 is elongate and tubular and extends from the proximal end 3102 to the distal end 3104 of the inner member 3100. The main body 3106 defines a seventh diameter $d_7$ extending directly from a first outer point 3110 of the outer surface 3114 to a second outer point 3112 of the outer surface 3114 opposite the first outer point 3110 about the longitudinal axis of the main body 3106. The main body 3106 is substantially rectangular in cross-sectional shape. It is noted, however, that the main body may have other cross-sectional shapes in alternative embodiments, including rectangular, elliptical, and substantially elliptical. A skilled artisan will be to determine a suitable cross-sectional shape for the main body according to a particular example based on various considerations, including the shape and size of the outer member and the shape and size of the inner member. In other embodiments, the main body may taper or widen from the proximal end to the distal end.

The proximal end 3102 includes a first portion 3120 and a second portion 3122. The first portion 3120 is not threaded; the second portion 3122 is threaded and designed to mate with a threaded portion of the outer member 3200, described below. Any portion of the proximal end 3102 may be threaded. A skilled artisan will be able to determine how to configure the proximal end according to a particular example based on various considerations, including the shape and size of the outer member and the shape and size of the inner member. In other embodiments, the proximal end may not be threaded at all and, instead, may define or include an different type of attachment, such as a snap-fit structure, that will enable the proximal end to mate with the outer member.

The distal end 3104 includes first and second split tabs 3140, 3142 configured to house the head 3902 of an anchor 3900. The first and second split tabs 3140, 3142 cooperatively define a distal opening 3144. In addition, the first split tab 3140 also defines a first outer surface 3150 and a first inner surface 3152 substantially opposite the first outer surface 3150. The second split tab 3142 defines a second outer surface 3154 and a second inner surface 3156 substantially opposite the second outer surface 3154. The first and second split tabs 3140, 3142 are flexible and, upon pressure from the head 3902 of an anchor 3900 as it enters the distal opening 3144, may move away from one another. Though this embodiment includes two split tabs 3140, 3142, in other embodiments any number of tabs may form the distal end. A skilled artisan will be able to determine the number of split tabs according to a particular example based on various considerations, including the shape and size of the inner member. Alternatively, three, four, five, six, or more than six split tabs may form the distal end. Additionally, the split tabs 3140, 3142 may be integrally formed with the main body 3106 of the inner member 3100, as illustrated herein, or the split tabs may be welded, adhesively attached, or otherwise attached to the main body of the inner member.

The first and second split tabs 3140, 3142 also define an eighth diameter $d_8$ extending directly from a first outer point 3146 disposed on the first outer surface 3150 and a second outer point 3148 disposed on the second outer surface 3154 opposite the first outer point 3146. The eighth diameter $d_8$ is greater than the seventh diameter $d_7$.

Figure 16:
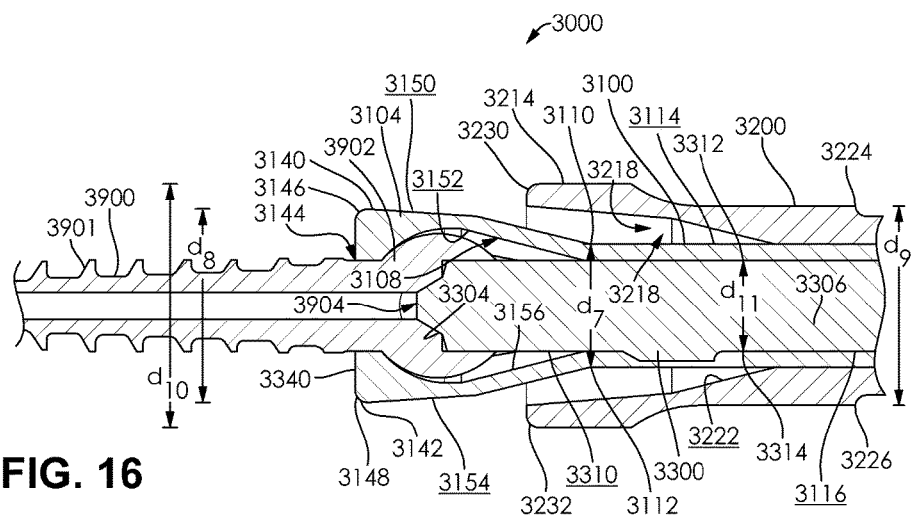
FIG. 16 is a magnified lengthwise cross-sectional view of Area IV of the driver and anchor illustrated in FIG. 14.
Figure 17:
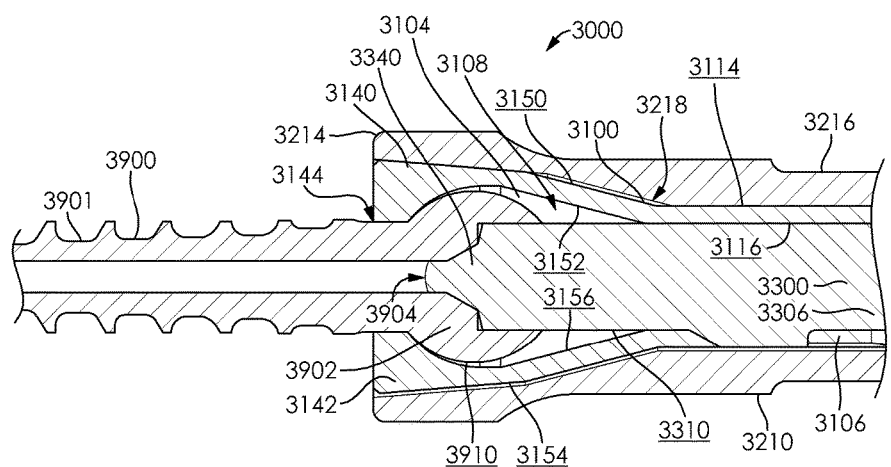
FIG. 17 is a magnified lengthwise cross-sectional view of Area V of the driver and anchor illustrated in FIG. 15.

The grasping member 3300 is best illustrated in FIGS. 16 and 17 and includes a proximal end (not illustrated in the FIGURES), a distal end 3304, a main body 3306 extending from the proximal end to the distal end 3304, and an outer surface 3310.

The main body 3306 of the grasping member 3300 defines an eleventh diameter $d_{11}$ extending directly from a first outer point 3312 of the outer surface 3310 to a second outer point 3314 of the outer surface 3310 opposite the first outer point 3312. In the illustrated embodiment, the eleventh diameter $d_{11}$ is less than the seventh diameter $d_7$. The main body 3306 is substantially rectangular in cross-sectional shape; it is noted, however, that the main body may have other cross-sectional shapes in alternative embodiments, including rectangular, elliptical, and substantially elliptical. A skilled artisan will be to determine a suitable cross-sectional shape for the main body of the grasping member based on various considerations, including the shape and size of the outer member and the shape and size of the inner member.

The distal end 3304 of the grasping member 3300 has a distal tip 3340 configured to engage with the head 3902 of a screw 3900. The distal tip 3340 is sized such that it mates with the recess 3904 of the head 3902 of the screw 3900 and will not allow the screw 3900 to become dislodged from the distal tip 3340 upon movement of the inner member 3100 until a user desires such dislodgement. Any structure may be used to engage the distal end with a screw. A skilled artisan will be able to determine how to configure the distal end of the grasping member according to a particular example based on various considerations, including the shape and size of the outer member and the shape and size of the inner member. In an alternative embodiment, the distal end of the grasping member may include a snap-fit structure to engage the head of an anchor. In a different embodiment, the distal end of the grasping member may be threaded to mate with threading defined by the head of a screw member.

In the illustrated embodiment, the outer surface 3310 of the grasping member 3300 is welded to the inner surface 3116 of the inner member 3100. The grasping member 3300 is not movable within the inner member 3300. The grasping member 3300 may be attached to the inner member 3100 in any manner. A skilled artisan will be able to how to attach the grasping member to the inner member according to a particular example based on various considerations, including the shape and size of the outer member and the shape and size of the inner member. In other embodiments, the grasping member may be attached to the inner member via adhesives, hooks, or any other suitable technique in other embodiments. Additionally, the grasping member may be integrally formed with the inner member in a different embodiment. In another alternative embodiment, the grasping member may be movable within the inner member.

FIGS. 13 through 17 also illustrate the outer member 3200. The outer member 3200 is comprised of a first piece 3210 and a second piece 3250.

The first piece 3210 of the outer member 3200 has a proximal end 3212, a distal end 3214, a main body 3216 extending from the proximal end 3212 to the distal end 3214, a lumen 3218 extending from the proximal end 3212 to the distal end 3214, and an outer surface 3220.

The main body 3216 of the first piece 3210 is elongate and tubular and is substantially rectangular in cross-sectional shape. The main body 3216 defines a ninth diameter $d_9$ extending directly from a first outer point 3224 of the outer surface 3220 to a second outer point 3226 of the outer surface 3220 opposite the first outer point 3224 about the longitudinal axis of the main body 3216. The ninth diameter $d_9$ is greater than the eighth diameter $d_8$ in this embodiment.

The distal end 3214 of the first piece 3210 is configured to house the distal end 3104 of the inner member 3100 and defines a tenth diameter $d_{10}$ extending directly from a third outer point 3230 of the outer surface 3220 to a fourth outer point 3232 of the outer surface 3220 opposite the third outer point 3230 about the longitudinal axis of the main body 3216. The tenth diameter $d_{10}$ is greater than the ninth diameter $d_9$ in this embodiment.

Figures 13, 14, 15:
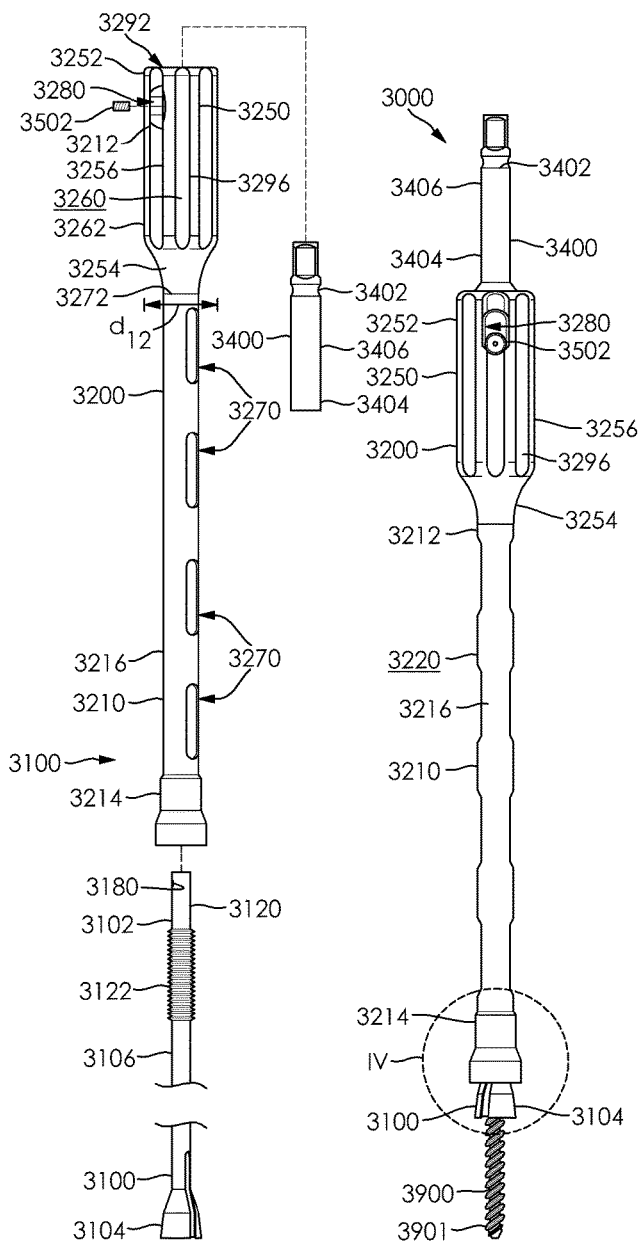
FIG. 13 is an exploded view of a first example driver.
FIG. 14 is a side view of the driver illustrated in FIG. 13 with an associated anchor. The driver is illustrated in a first configuration.
FIG. 15 is a side view of the driver and anchor illustrated in FIG. 14. The driver is illustrated in a second configuration.

Optionally, the main body 3216 of the first piece 3210 may define one or more fenestrations 3270. As best illustrated in FIGS. 13 and 15, in the illustrated embodiment the main body 3216 defines four fenestrations 3270. The fenestrations 3270 are rounded rectangular in shape and are arranged in a row. Furthermore, any fenestrations included may be aligned in any configuration and have any shape. A skilled artisan will be able to determine whether to include fenestrations and how to align the fenestrations according to a particular example based on various considerations, including the shape and size of the inner member. In other embodiments, though, zero, one, two, three, five, or more than five fenestrations may be included.

The second piece 3250 of the outer member 3200 has a proximal end 3252, a distal end 3254, a main body 3256 extending from the proximal end 3252 to the distal end 3254, a lumen (not illustrated in the FIGURES) extending from the proximal end 3252 to the distal end 3254, an outer surface 3260, and an inner surface (not illustrated in the FIGURES). The second piece 3250 is also rotatable about its longitudinal axis.

The main body 3256 of the second piece 3250 is elongate and tubular and defines a twelfth diameter $d_{12}$ extending directly from a first outer point 3262 of the outer surface 3260 to a second outer point 3264 of the outer surface 3260 opposite the first outer point 3262 about the longitudinal axis of the main body 3256. In the illustrated embodiment, the twelfth diameter $d_{12}$ is greater than the tenth diameter $d_{10}$.

Additionally, the main body 3256 of the second piece 3250 defines ridges 3296 that assist in gripping the main body 3256. However, any structure can be included on the main body 3256 to assist gripping. A skilled artisan will be able to determine whether to include gripping structures and what type of gripping structure should be included according to a particular example based on various considerations, including the shape and size of the second piece. In other embodiments, the main body may also define grooves, protrusions, or any other structure that assists in gripping the main body. The main body may also not define any structures that assist in gripping the main body.

The main body 3256 of the second piece 3250 defines a passageway 3280 configured to allow the insertion of a connecting screw 3502. The connecting screw 3502 is inserted through the passageway 3280 and into a screw hole 3180 defined by the inner member 3100. Insertion of the connecting screw 3502 into the screw hole 3180 attaches the inner member 3100 to the cap 3400. Any suitable connecting means may be used, however. A skilled artisan will be to determine how to attach the inner member to the cap the according to a particular example based on various considerations, including the shape and size of the first piece and the shape and size of the inner member. For example, the inner member may be attached to the cap by a snap-fit structure, threading, welding, or any other suitable technique.

The distal end 3254 of the second piece 3250 has the same diameter as the proximal end 3212 of the first piece 3210 at its most distal point 3270 and has the same diameter as the main body 3256 of the second piece 3250 at its most proximal point 3272. Thus, the distal end 3254 of the second piece 3250 tapers distally. A skilled artisan will be to determine a suitable diameter or suitable diameters of the distal end of the second piece according to a particular example based on various considerations, including the shape and size of the first piece and the shape and size of the inner member. In other embodiments, though, the distal end may have any other diameter and, furthermore, may or may not include a proximal taper or a distal taper.

The inner surface (not illustrated in the FIGURES) of the proximal end 3252 of the second piece 3250 defines a threaded portion (not illustrated in the FIGURES) designed to mate with the second portion 3122, which is threaded, of the inner member 3100. Additionally, the proximal end 3252 defines a proximal opening 3292. In other embodiments, the inner surface may not be threaded, but instead may include a snap-fit structure, hook, or other mechanism of mating with the second portion of the inner member.

In the illustrated embodiment, the first piece 3210 and second piece 3250 are welded together to form the outer member 3200. More specifically, the distal end 3254 of the second piece 3250 is welded to the proximal end 3212 of the first piece 3210. The first and second pieces may be attached in any way, however. A skilled artisan will be to determine how to attach the first and second pieces according to a particular example based on various considerations, including the shape and size of the first piece and the shape and size of the second piece. In different embodiments, the first piece may be attached to the second piece via a mechanical attachment, adhesives, or any other suitable technique. In other embodiments, the first and second pieces may be integrally formed.

Optionally, the driver 3000 may also include a cap 3400 that is attached to the second portion 3122 of the proximal end 3102 of the inner member 3100 via threads. The cap 3400 has a proximal end 3402, a distal end 3404, and a main body 3406 extending from the proximal end 3402 to the distal end 3404. The main body 3406 is elongate and tubular. The distal end 3404 is configured to mate with the proximal end 3102 of the inner member 3100 to allow automatic rotation of the device within the outer member 3200.

In use, and described in greater detail below, the inner member 3100 is movably disposed within the outer member 3200. The inner member 3100 is not captive within the outer member 3200. FIGS. 14 and 16 illustrate the driver 3000 in a first configuration; FIGS. 15 and 17 illustrate the driver 3000 is a second configuration. In the first configuration, each of the distal end 3104 of the inner member 3100 and the distal end 3304 of the grasping member 3300 is disposed outside of the distal end 3214 of the first piece 3210 of the outer member 3200. As such, the head 3902 of the screw member 3900 is also disposed outside of the distal end 3214 of the first piece 3210 of the outer member 3200 in this configuration. A skilled artisan will be able to determine the precise placement of the distal ends of the inner and grasping members in relation to the outer member according to a particular example based on various considerations, including the shape and size of the inner member and the shape and size of the outer member. In an alternative embodiment, one or both of the distal end of the inner member and distal end of the grasping member may be partially disposed within the distal end of the first piece of the outer member when the driver is in the first configuration.

The driver 3000 is transitioned from the first configuration to the second configuration through the rotation of the second piece 3250 of the outer member 3200. Upon rotation of the second piece 3250 of the outer member 3200, the threaded second portion 3122 of the proximal end 3102 of the inner member 3100 mates with the threaded portion of the inner surface (not illustrated in the FIGURES) of the second piece 3250 to move the inner member 3100 is the proximal direction. Thus, the main body 3106 of the inner member 3100 moves proximally through the proximal opening 3292 of the second piece 3250. At the same time, the distal end 3104 of the inner member 3100 and the distal end 3304 of the grasping member 3300 are moved in the proximal direction such that when the driver 3000 is in the second configuration, the entire distal end 3104 of the inner member 3100 and the entire distal end 3304 of the grasping member 3300 are disposed within the distal end 3214 of the first piece 3210 of the outer member 3200. As such, the head 3902 of the screw member 3900 is also disposed within the distal end 3214 of the first piece 3210 of the outer member 3200 in this configuration. A skilled artisan will be able to determine the precise placement of the distal ends of the inner and grasping members in relation to the outer member according to a particular example based on various considerations, including the shape and size of the inner member and the shape and size of the outer member. In an alternative embodiment, one or both of the distal end of the inner member and distal end of the grasping member may be partially disposed within the distal end of the first piece of the outer member when the driver is in the first second.

Each of FIGS. 18, 19, 20, 21, 22, and 23 illustrates a set screw driver 5000 or one or more components thereof. The set screw driver 5000 includes an inner member 5100, an outer member 5200, and a connecting screw 5300. The inner member 5100 is rotatably disposed within the outer member 5200.

The inner member 5100 has a proximal end 5102, a distal end 5104, a main body 5106 extending from the proximal end 5102 to the distal end 5104, and an outer surface 5114.

The main body 5106 is elongate and tubular and includes a mating portion 5108 configured to contact the connecting screw 5300. The mating portion 5108 defines a first radius (not illustrated in the FIGURES) extending from a first mating portion point 5160 disposed on the surface of the mating portion 2108 to the longitudinal axis (not illustrated in the FIGURES) of the inner member 5100. The main body 5106 defines a second radius (not illustrated in the FIGURES) extending from a first main body point 5162 disposed on the main body to the longitudinal axis of the inner member 5100. The proximal end 5102 defines a third radius (not illustrated in the FIGURES) extending from a first proximal point 5164 disposed on the surface of the proximal end 5102 to the longitudinal axis of the inner member 5100. The distal end 5104 defines a fourth radius $r_4$ extending from a first distal point 5166 disposed on the distal end 5104 to the longitudinal axis of the inner member 5100. The first radius is less than each of the second, third, and fourth radii. Furthermore, the third radius is greater than the fourth radius, and the fourth radius is about equal to the second radius. A skilled artisan will be able to determine suitable first, second, third, and fourth radii according to a particular example based on various considerations, including the shape and size of the a set screw that is used with the set screw driver and the shape and size of the outer member. In an alternative embodiment, the third and fourth radii may be equal to one another. In another embodiment, the inner member may define a single radius from the proximal end to the distal end.

The distal end 5104 of the inner member 5100 also defines a first threaded portion 5130. The first threaded portion 5130 begins at the distal end 5104 and extends in the proximal direction. The first threaded portion 5130 is configured to mate with a set screw (described and illustrated below). The first threaded portion 5130 is integrally formed with the distal end 5104 of the inner member 5100 in the illustrated embodiment. A skilled artisan will be able to determine a suitable structure to include on the distal end according to a particular example based on various considerations, including the shape and size of the set screw and the shape and size of the outer member. In an alternative embodiment, a snap-fit structure configured to mate with a set screw may be directly or indirectly attached to the distal end. In a different embodiment, a hook or another mechanical structure configured to mate with a set screw that is coated with an adhesive may be directly or indirectly attached to the distal end.

FIGS. 18 through 23 also illustrate the outer member 5200. The outer member 5200 includes a proximal end 5202, a distal end 5204, a main body 5206 extending from the proximal end 5202 to the distal end 5204, a lumen 5208 extending from the proximal end 5202 to the distal end 5204, an inner surface 5212, and an outer surface 5214.

The main body 5206 of the outer member 5200 is elongate and tubular and defines two rows of fenestrations 5252. Each of the fenestrations 5252 is rounded rectangular in shape and extends from the outer surface 5214 of the outer member 5200 to the inner surface 5212 of the outer member 5200. The main body may define any number of fenestrations, which may have any shape and any alignment. A skilled artisan will be able to determine a suitable number of fenestrations and a suitable configuration for the fenestrations according to a particular example based on various considerations, including the shape and size of the inner member and the shape and size of the outer member. In alternative embodiments, the main body may define zero, one, three, or more than three rows of fenestrations. In other embodiments, the main body may define zero, one two, three, four, five, seven, or more than seven fenestrations per row. In addition, different embodiments will include one or more fenestrations that are not configured in rows.

The main body 5206 defines a fifth radius (not illustrated in the FIGURES) extending from a first main body point 5260 disposed on the main body 5206 to the longitudinal axis (not illustrated in the FIGURES) of the outer member 5200. The proximal end 5202 defines a sixth radius extending from a first proximal point 5262 disposed on the proximal end 5202 to the longitudinal axis of the outer member 5200. The distal end 5204 defines a seventh radius extending from a first distal point 5264 disposed on the distal end 5204 to the longitudinal axis of the outer member 5200. The seventh radius is less than each of the fifth and sixth radii. Furthermore, the sixth radius is greater than the fifth radius. A skilled artisan will be able to determine suitable fifth, sixth, and seventh radii according to a particular example based on various considerations, including the shape and size of the a set screw that is used with the set screw driver and the shape and size of the inner member. In an alternative embodiment, the fifth and seventh radii may be equal to one another. In another embodiment, the outer member may define a single radius from the proximal end to the distal end.

The proximal end 5202 of the outer member 5200 defines a connecting screw passageway 5218 extending from the inner surface 5212 to the outer surface 5214 of the outer member 5200. The connecting screw passageway 5218 is configured to allow for the insertion of at least a portion of a connecting screw 5300. The proximal end 5202 also defines a proximal opening 5222. A skilled artisan will be able to determine how to suitably configure the connecting screw passageway according to a particular example based on various considerations, including the shape and size of the inner member and the shape and size of the connecting screw. In alternative embodiments, the connecting screw passageway may be configured to allow for the insertion of devices other than connecting screws, such as rods, bolts, nails, or other connecting devices.

The proximal end 5202 of the outer member 5200 also includes gripping ridges 5224 that aid in the handling of the outer member 5200. The proximal end 5202 may define any number of gripping ridges 5224. A skilled artisan will be able to determine whether to include gripping ridges or other structures that aid in the handling of the outer member according to a particular example based on various considerations, including the shape and size of the inner member and the shape and size of the outer member. In other embodiments, the proximal end may define a series of bumps, a handle, one or more indentations, or any other structure in place of the gripping ridges to aid in the handling of the outer member.

Figure 21:
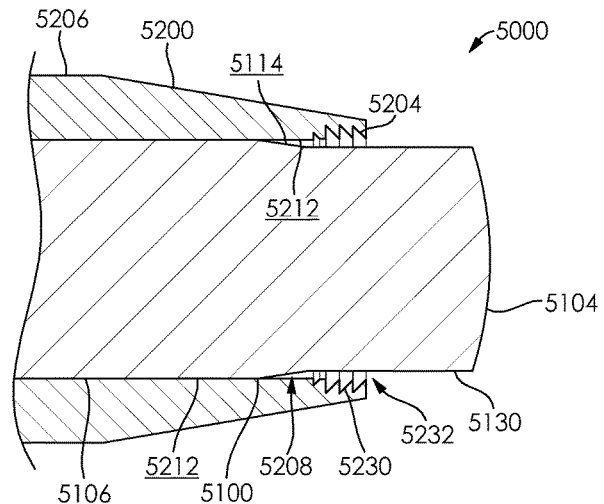
FIG. 21 is a magnified view of Area VI of the set screw driver illustrated in FIG. 20.

As best illustrated in FIG. 21, the distal end 5204 includes a second threaded portion 5230 that is defined by the inner surface 5212 of the outer member 5200 and extends in the proximal direction. The second threaded portion 5230 is configured to mate with a set screw (described and illustrated below). The distal end 5204 also defines a distal opening 5232. The second threaded portion 5230 is integrally formed with the distal end 5204 of the outer member 5200 in the illustrated embodiment. Any suitable structure may be used, however. A skilled artisan will be able to determine a suitable structure to include on the distal end according to a particular example based on various considerations, including the shape and size of the inner member and the shape and size of the set screw. In an alternative embodiment, a snap-fit structure configured to mate with a set screw may be directly or indirectly attached to the distal end. In a different embodiment, a hook or another mechanical structure configured to mate with a set screw that is coated with an adhesive may be directly or indirectly attached to the distal end.

The connecting screw 5300 includes a head 5302 and a shaft 5304.

The inner member 5100 is rotatably disposed within the outer member 5200. The main body 5106 of the inner member 5100 is housed within the lumen 5208 of the outer member 5200 such that the proximal end 5102 of the inner member 5100 is disposed proximal to the proximal opening 5222 and the distal end 5104 of the inner member 5100 is disposed distal to the distal opening 5232. The shaft 5304 of the connecting screw 5300 extends through the connecting screw passageway 5218 such that it is in contact with the mating portion 5108 of the main body 5106. The connecting screw 5300, thus, holds the inner member 5100 in place within the outer member 5200; the inner member 5100 cannot move proximally or distally due to the presence of the connecting screw 5300 in this embodiment. The inner member 5100, however, is still rotatable within the outer member 5200 when the connecting screw 5300 is in contact with the inner member 5100. A skilled artisan will be able to determine how to suitably configure the inner member, outer member, and connecting screw according to a particular example based on various considerations, including the shape and size of the inner member and the shape and size of the outer member. In an alternative embodiment, the connecting screw allows both proximal and distal movement of the inner member. In a different embodiment, connecting screw prevents the inner member from rotating within the outer member. In another embodiment, the connecting screw prevents proximal, distal, and rotational movement of the inner member within the outer member.

FIGS. 22 and 23 illustrate the set screw driver 5000 described and illustrated above, and a set screw 5400. The set screw 5400 includes a proximal end 5402, a distal end 5404, a and main body 5406 extending from the proximal end 5402 to the distal end 5404.

The proximal end 5402 of the set screw 5400 defines a proximal opening 5422. The proximal opening 5422 is substantially rectangular in cross-sectional shape. The proximal opening may have any suitable shape however. A skilled artisan will be able to determine a suitable cross-sectional shape of the proximal opening according to a particular example based on various considerations, including the shape and size of the inner member and the shape and size of the outer member. In other embodiments, however, the proximal opening may have any cross-sectional shape, including square, triangular, circular, and elliptical.

The main body 5406 defines a channel 5450 extending from the proximal opening 5422 to the base 5452 of the channel 5450. The main body 5406 also defines an inner surface 5456 extending from the base 5452 of the channel 5450 to the proximal opening 5422. The inner surface 5456 defines a first threaded portion 5440 configured to mate with the first threaded portion 5130 of the distal end 5104 of the inner member 5100, as illustrated in FIG. 23. A skilled artisan will be able to determine how to configure the inner surface of the main body of the set screw according to a particular example based on various considerations, including the shape and size of the inner member and the shape and size of the outer member. In an alternative embodiment, the inner surface of the main body of the set screw may define a snap-fit structure, a hook, or a section having an adhesive coating configured to mate with the distal end of the inner member.

The main body 5406 also defines an outer surface 5460. The outer surface 5460 defines second and third threaded portions 5462, 5464. The second threaded portion 5462 is disposed proximal to the third threaded portion 5464 and has a smaller diameter (not illustrated in the FIGURES) than the diameter (not illustrated in the FIGURES) of the third threaded portion 5464.

The second threaded portion 5462 is configured to mate with the second threaded portion 5230 of the inner surface 5212 of the distal end 5204 of the outer member 5200, as best illustrated in FIG. 23. The third threaded portion 5464 is configured to mate with a head member, such as the head member 3800 described above.

In use, and described in greater detail below, the first threaded portion 5130 of the distal end 5104 of the inner member 5100 is rotated via rotational force on the proximal end 5102 of the inner member 5100 such that the distal end 5104 of the inner member 5100 mates with the first threaded portion 5440 of the inner surface 5456 of the main body 5406 of the set screw 5400. Continued rotational force on the proximal end 5102 of the inner member 5100 advances the set screw 5400 proximally such that the second threaded portion 5462 of the outer surface 5460 of the set screw 5400 mates with the second threaded portion 5230 of the inner surface 5212 of the distal end 5204 of the outer member 5200. Rotational force on the proximal end 5102 of the inner member 5100 ultimately advances at least a portion of the set screw 5400 within the lumen 5208 of the outer member 5200. A skilled artisan will be able to determine how to suitably advance the set screw into the lumen of the outer member according to a particular example based on various considerations, including the shape and size of the inner member and the shape and size of the outer member. Alternatively, a proximally-directed or distally-directed force may advance the set screw proximally on the inner member or the outer member, respectively. Additionally, in other embodiments, the entire set screw may be housed within the lumen of the outer member after rotational force has been applied to the proximal end of the inner member or no portion of the set screw may be housed within the lumen of the outer member after rotational force has been applied to the proximal end of the inner member.

Figure 7:
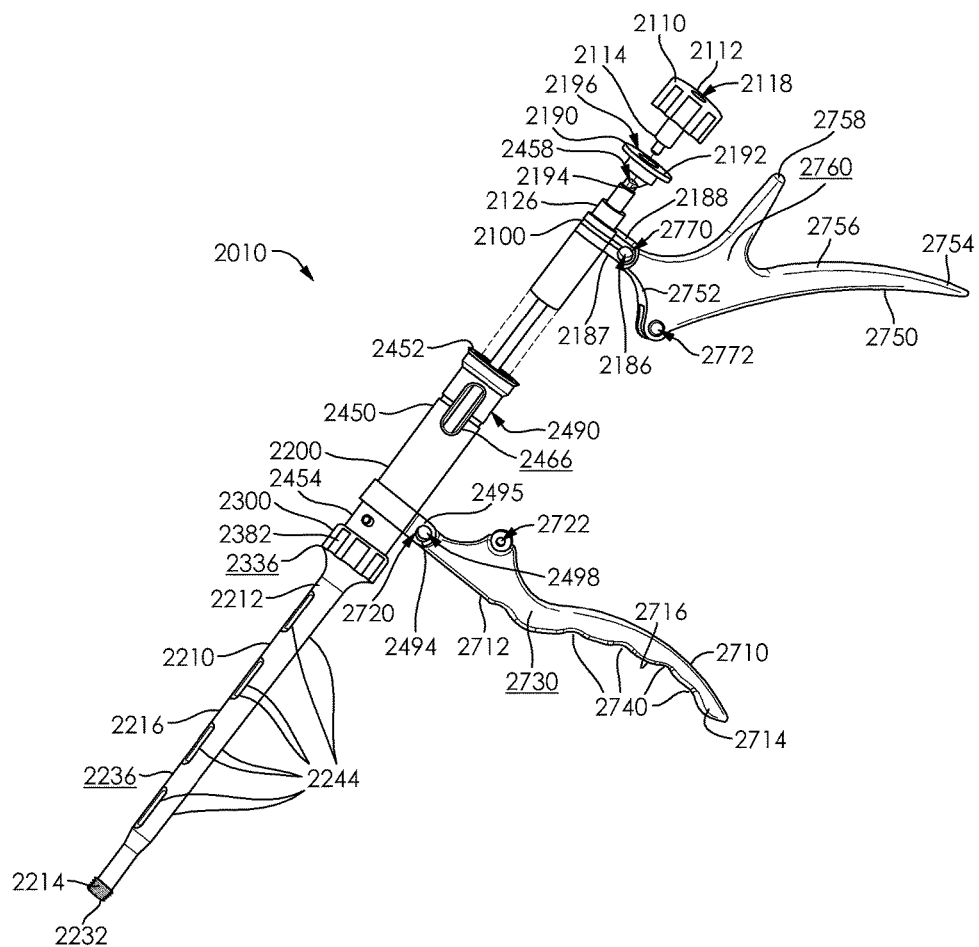
FIG. 7 is an exploded view of another example anchor assembly tool.
Figure 24:
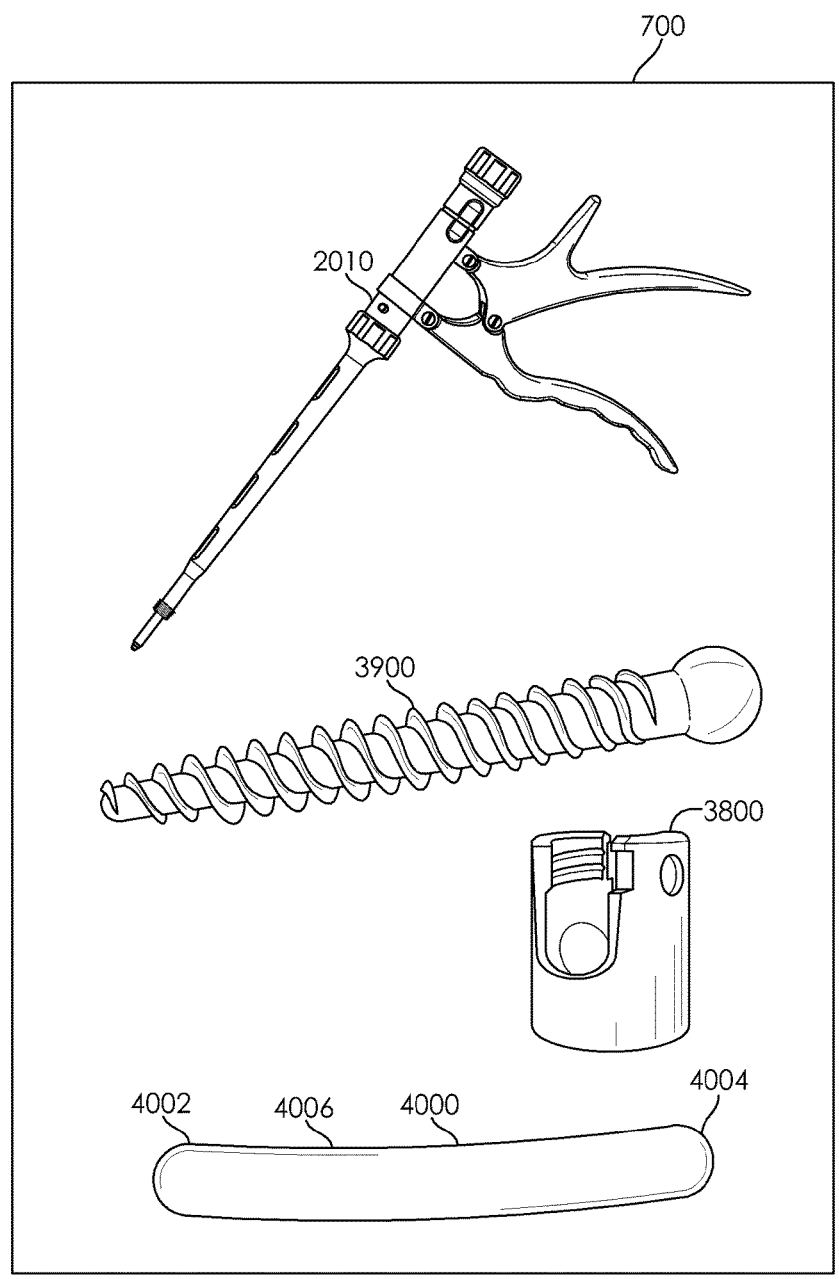
FIG. 24 illustrates a schematic illustration of an example kit.

FIG. 24 illustrates an example kit 700 comprising an anchor assembly tool according to an example embodiment, such as anchor assembly tool 2010 illustrated, for example, in FIG. 7; an anchor according to an embodiment, such as anchor 3900, illustrated in, for example, FIG. 12A; and a head member according to an embodiment, such as head member 3800, illustrated in, for example, FIG. 12A.

The kit also includes a rod 4000. The rod 4000 is an elongate member comprising a main body 4006 extending between proximal and distal ends 4002, 4004. The main body 4006 is substantially cylindrical in shape.

While a single anchor assembly tool 2010 is illustrated in FIG. 24, a plurality of anchor assembly tools may be included in the kit, as well. In addition, more than one anchor may be included in kit 700; these anchors may have different sizes and shapes. Multiple head members may also be included in the kit 700, and each head member may be sized and shaped differently than any other head member. In addition, other tools or devices such as a rod insertion device may also be included in the kit. A skilled artisan will be able to select a suitable number of anchor assembly tools, anchors, and head members for inclusion in a kit according to a particular example based on various considerations, including the sizes and shapes of the anchor assembly tools, anchors, and head members.

Figure 25:
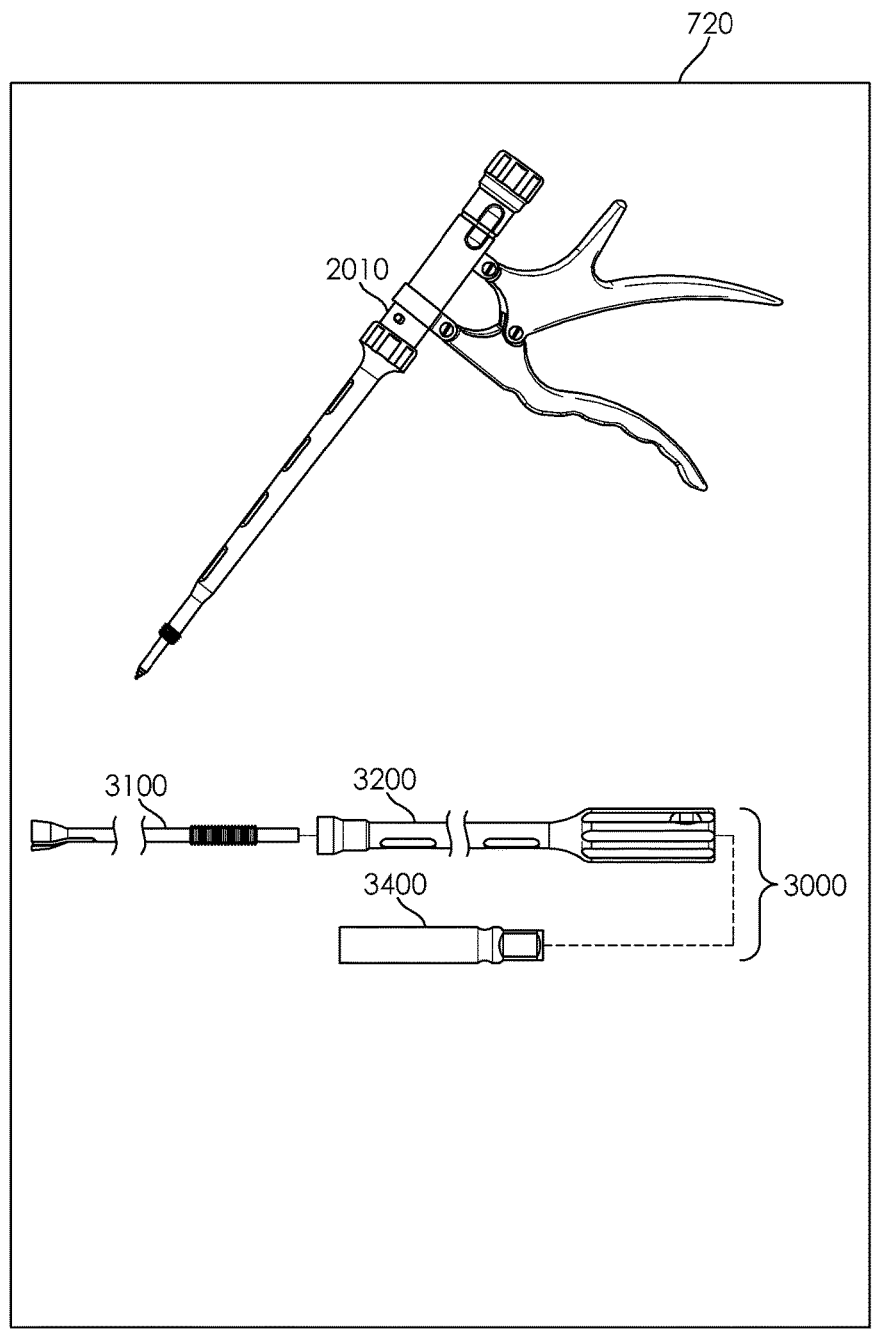
FIG. 25 illustrates a schematic illustration of another example kit.

FIG. 25 illustrates another example kit 720 comprising an anchor assembly tool according to an example embodiment, such as anchor assembly tool 2010 illustrated, for example, in FIG. 7 and a driver according to an example embodiment, such as driver 3000 illustrated, for example, in FIG. 13.

While a single anchor assembly tool 2010 and a single driver 3000 are illustrated in FIG. 25, a plurality of anchor assembly tools and drivers may be included in the kit, as well. In addition, one or more anchors, head members, or rods may also be included in the kit. A skilled artisan will be able to select a suitable number of anchor assembly tools, drivers, anchors, head members, and rods according to a particular example based on various considerations, including the sizes and shapes of the anchor assembly tools, anchors, and head members.

Figure 26:
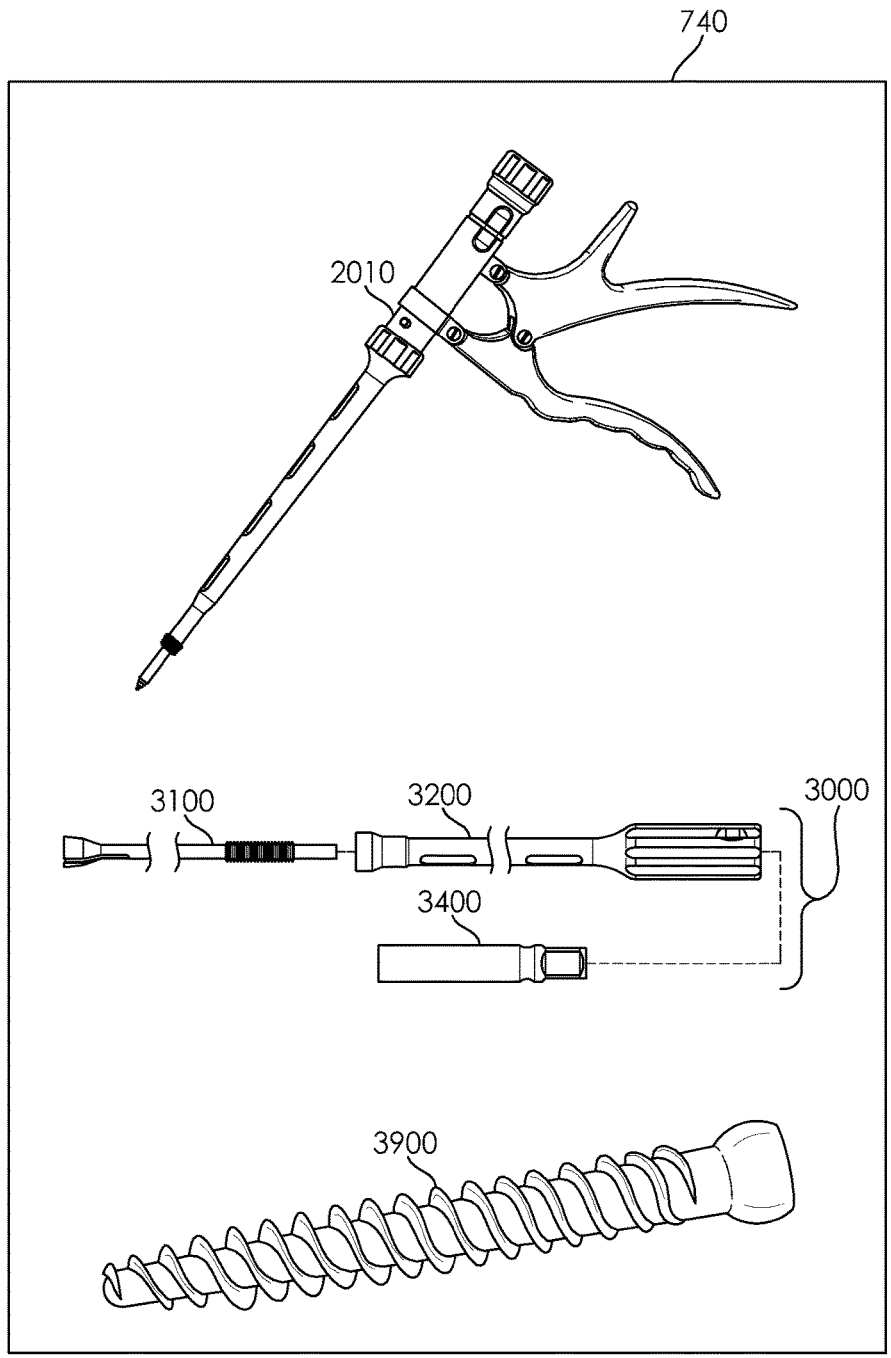
FIG. 26 illustrates a schematic illustration of another example kit.

FIG. 26 illustrates another example kit 740 comprising an anchor assembly tool according to an example embodiment, such as anchor assembly tool 2010 illustrated, for example, in FIG. 7; a driver according to an example embodiment, such as driver 3000 illustrated, for example, in FIG. 13; and an anchor according to an embodiment, such as anchor 3900, illustrated in, for example, FIG. 12A.

While a single anchor assembly tool 2010, a single driver 3000, and a single anchor 3900 are illustrated in FIG. 26, a plurality of anchor assembly tools, drivers, and anchors may be included in the kit, as well. In addition, one or more head members or rods may also be included in the kit. A skilled artisan will be able to select a suitable number of anchor assembly tools, drivers, anchors, head members, and rods according to a particular example based on various considerations, including the sizes and shapes of the anchor assembly tools, anchors, and head members.

Figure 18:
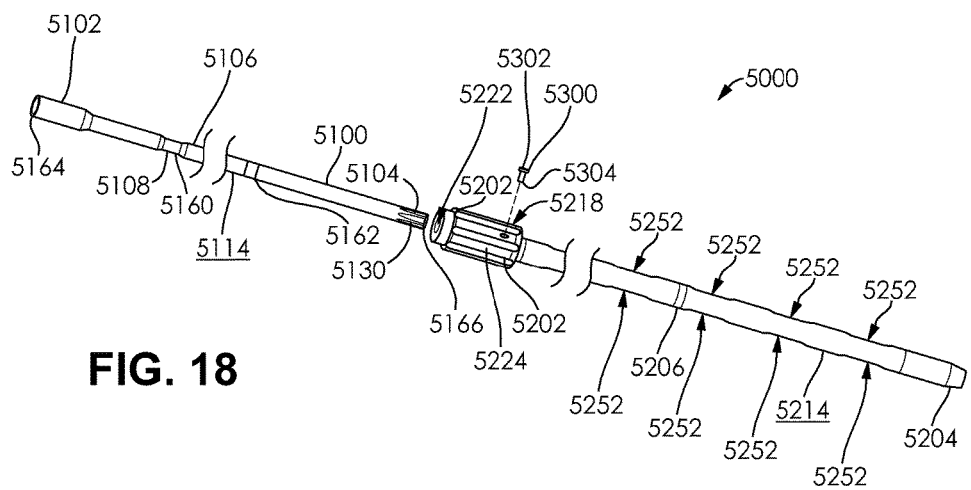
FIG. 18 is an exploded view of a first example set screw driver.
Figure 19:
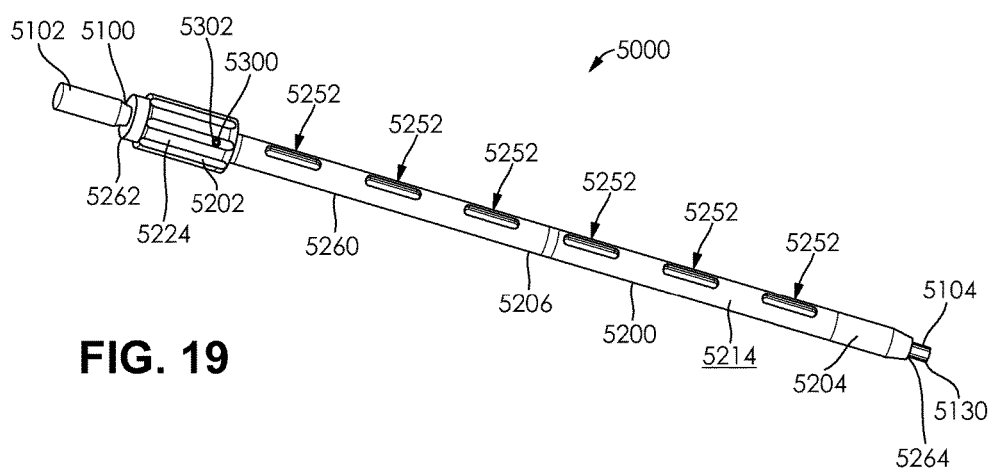
FIG. 19 is a perspective view of the set screw driver illustrated in FIG. 18.
Figure 20:
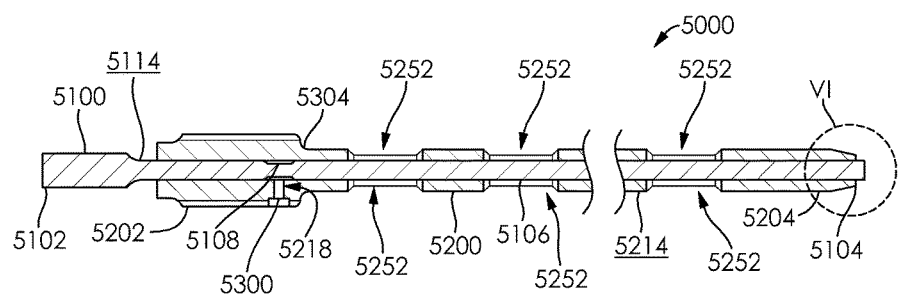
FIG. 20 is a cross-sectional view of the set screw driver illustrated in FIG. 19 taken along its lengthwise axis.
Figure 27:
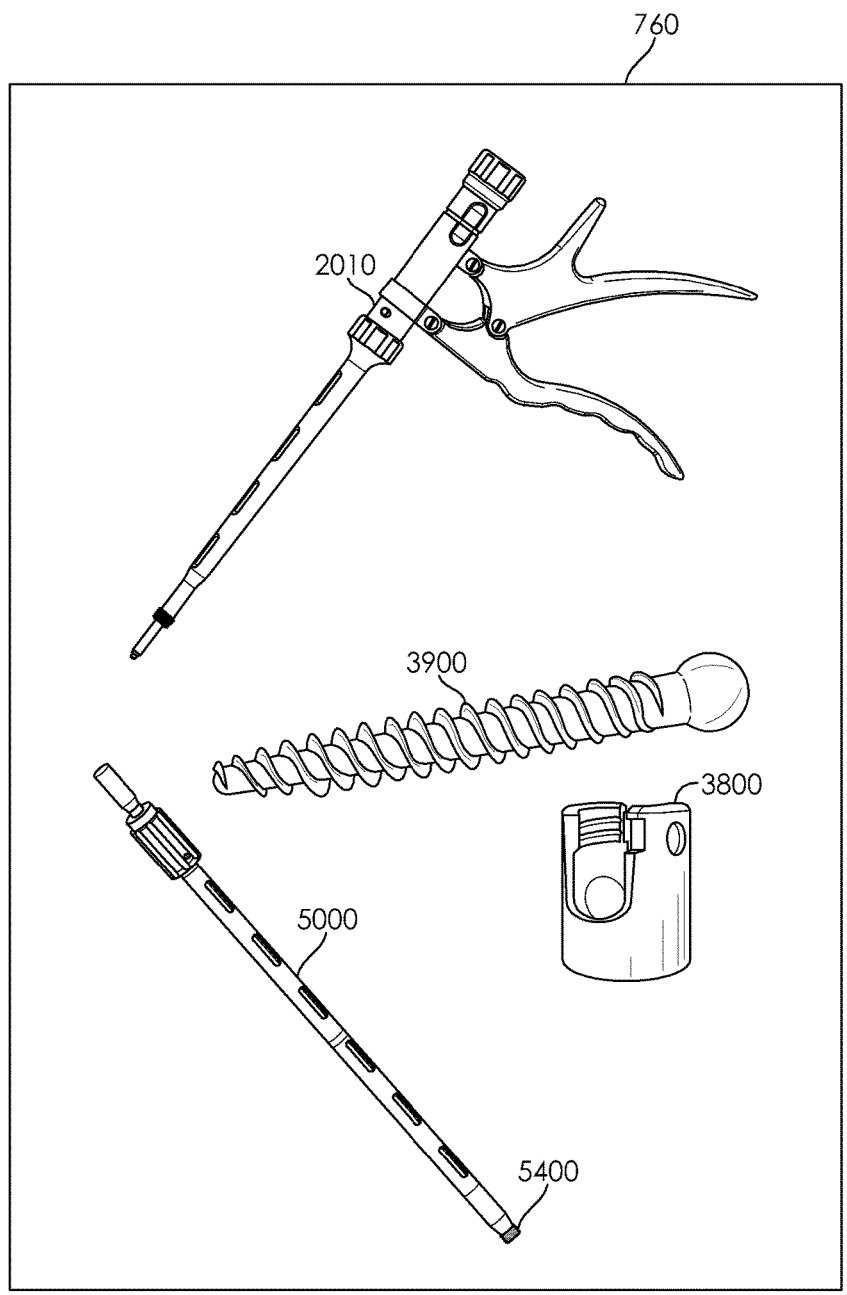
FIG. 27 illustrates a schematic illustration of another example kit.

FIG. 27 illustrates another example kit 760 comprising an anchor assembly tool according to an example embodiment, such as anchor assembly tool 2010, illustrated in, for example, FIG. 7; an anchor according to an embodiment, such as anchor 3900, illustrated in, for example, FIG. 12A; a head member according to an embodiment, such as head member 3800, illustrated in, for example, FIG. 12A; a set screw driver according to an embodiment, such as set screw driver 5000, illustrated in, for example, FIG. 18; and a set screw according to an embodiment, such as set screw 5400, illustrated in, for example, FIG. 22.

While a single anchor assembly tool 2010, a single anchor 3900, a single head member 3800, a single set screw driver 5000, and a single set screw 5400 are illustrated in FIG. 27, a plurality of anchor assembly tools, anchors, head members, set screw drivers, and set screws may also be included in the kit. A skilled artisan will be able to select a suitable number of anchor assembly tools, drivers, anchors, head members, and rods according to a particular example based on various considerations, including the sizes and shapes of the anchor assembly tools, anchors, and head members.

Figure 28:
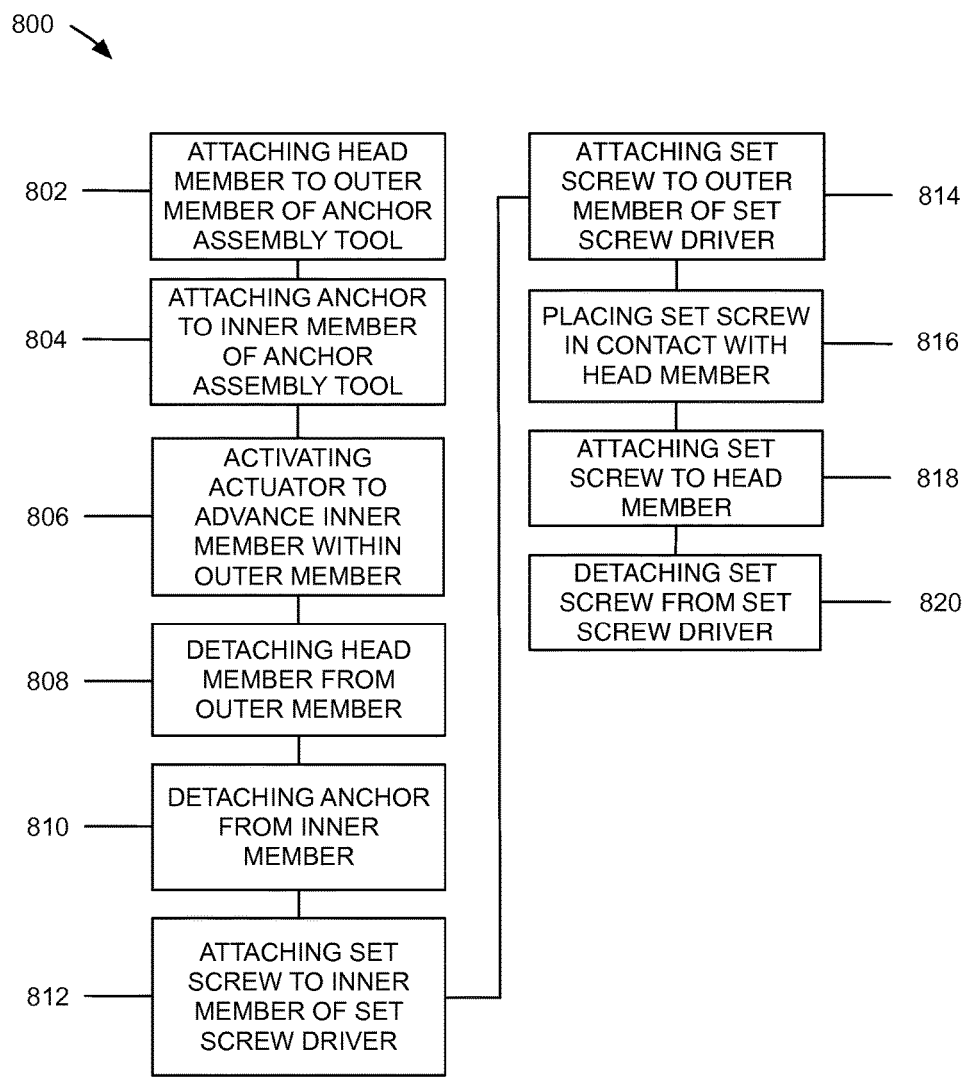
FIG. 28 is a flowchart representation of an example method of assembling an anchor assembly.

FIG. 28 is a flowchart representation of an example method 800 of installing an anchor into a head member, such as an anchor as described herein. Performance of the method results in the insertion of an anchor into a head member. This method can be used for installing any type of anchor into any type of head member. An example method includes the use of a bone anchor and its corresponding head member.

An initial step 802 comprises releasably attaching a head member to an anchor assembly tool. Anchor assembly tool 1010 and head member 3800 are described in this step and the head member 3800 is releasably attached to the second threaded portion 1232 of the distal end 1224 of the outer member 1200. The anchor assembly tool may comprise any of the anchor assembly tools 10, 2010, 3010 described above and illustrated, or any other anchor assembly tool. The head member may comprise any head member, as well. Any suitable anchor assembly tool can be used to perform this step.

Another step 804 comprises releasably attaching an anchor to the first threaded portion 1132 of the distal end 1124 of the inner member 1100 of an anchor assembly tool 1010. Anchor 3900 is described in this step. The anchor may comprise any anchor, however.

Another step 806 comprises activating the actuator 1110 of the inner member 1100 to advance the inner member 1100 within the outer member 1200 such that the anchor 3900 is disposed within the head member 3800. Force on the activator 1110 occurs in this step. However, there are other ways to advance the inner member within the outer member such that the anchor is disposed within the head member. In another embodiment, for example, a handle may be attached to the anchor assembly tool and activation of the handle may result in advancement of the inner member within the outer member or the outer member over the inner member.

Another step 808 comprises detaching the head member 3800 from the second threaded portion 1232 of the distal end 1224 of the outer member 1200 of the anchor assembly tool 1010.

Another step 810 comprises detaching the anchor 3900 from the first threaded portion 1132 of the distal end 1124 of the inner member 1100 of the anchor assembly tool 1010.

In alternative methods, one or more of steps 812, 814, 816, 818, and 820 (discussed below) may be included in the example method 800, as well. Each of these steps is optional, however.

Optional step 812 comprises attaching a set screw to the inner member of a set screw driver. Set screw 5400 and set screw driver 5000 are described in this step and the set screw 5400 is releasably attached to the inner member 5100 of the set screw driver 5000. More specifically, the application of rotational force to the inner member 5100 of the set screw driver 5000 releasably attaches the first threaded portion 5440 of the inner surface 5456 of the main body 5406 of the set screw 5400 to the first threaded portion 5130 of the distal end 5104 of the inner member 5100 of the set screw driver 5000. Alternatively, the set screw may comprise any set screw and the set screw driver may comprise any set screw driver.

Another optional step 814 comprises applying rotational force to the inner member 5100 of the set screw driver 5000 until the set screw 5400 becomes releasably attached to the outer member 5200 of the set screw driver 5000. More specifically, the application of rotational force to the inner member 5100 of the set screw driver 5000 releasably attaches the second threaded portion 5462 of the outer surface 5460 of the set screw 5400 to the second threaded portion 5230 of the inner surface 5212 of the distal end 5204 of the outer member 5200 of the set screw driver 5000. Alternatively, however, distally-directed force on the outer member may releasably attach the set screw to the outer member of the set screw driver. In another method, proximally-directed force on the inner member may releasably attach the set screw to the outer member of the screw driver.

Another optional step 816 comprises placing the set screw 5400 in contact with the head member 3800.

Another optional step 818 comprises applying rotational force to the inner member 5100 of the set screw driver 5000 until the set screw 5400 becomes releasably attached to the head member 3800. More specifically, the application of rotational force to the inner member 5100 of the set screw driver 5000 releasably attaches the third threaded portion 5464 of the outer surface 5460 of the set screw 5400 to the head member threaded portion 3814 of the inner surface 3812 of the head member 3800. Alternatively, proximally-directed or distally-directed force on the inner member may releasably attach the third threaded portion of the outer surface to any portion of the main body of the head member.

Another optional step 820 comprises applying rotational force in the opposite direction as the rotational force described in optional step 818 to the inner member 5100 of the set screw driver 5000. This rotational force detaches the inner member 5100 and the outer member 5200 of the set screw driver 5000 from the set screw 5400. Alternatively, proximally-directed or distally-directed force on the inner member may detach the set screw from the set screw driver.

It is noted that it is considered advantageous to complete the method 800 in the order illustrated and described. However, any order is considered suitable.

All components of the anchor assembly tools, anchor-related tools, head members, anchors, and set screws can be made from any suitable material. Non-limiting examples of suitable materials include metals, such as stainless steel, titanium, cobalt-chromium, and other metals, and plastics commonly used in medical devices. Non-limiting examples of materials considered specifically suitable for use in the anchor assembly tools and drivers include Nitinol and other superelastic materials, polyurethane materials, silicone materials, and polyether ether ketone (PEEK) materials.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is to be given the full breadth of the appended claims and any and all equivalents thereof.

We claim:

1. An anchor assembly tool configured to engage a head member and an anchor, comprising:
    an outer member having an elongate, tubular main body, a proximal end, a distal end, a longitudinal axis, and a lumen extending from the proximal end to the distal end, the distal end configured to be releasably attached to said head member; and
    an inner member having an elongate, tubular main body and an actuator, the main body having a proximal end and a distal end, the inner member movably disposed within the lumen of the outer member, the actuator capable of advancing the inner member within the outer member, the actuator disposed on the proximal end of the main body, the distal end configured to be releasably attached to said anchor;
    wherein the distal end of the outer member operates independently from the distal end of the inner member;
    wherein activation of the actuator moves the inner member a predetermined distance relative to the longitudinal axis from a first configuration to a second configuration;
    wherein the distal end of the outer member and the distal end of the inner member cooperatively define a first distance extending from the distal end of the outer member to the distal end of the inner member when the inner member is in the first configuration;
    wherein the distal end of the outer member and the distal end of the inner member cooperatively define a second distance extending from the distal end of the outer member to the distal end of the inner member when the inner member is in the second configuration; and wherein the first distance is greater than the second distance; and wherein the distal end of the inner member defines a first snap-fit structure.

2. The anchor assembly tool of claim 1, wherein the distal end of the outer member defines a second snap-fit structure.

3. The anchor assembly tool of claim 2, wherein the proximal end of the outer member defines a cap; and wherein the cap defines a first side and a second side that is substantially opposite the first side.

4. The anchor assembly tool of claim 3, wherein the cap defines a channel extending from the first side to the second side.

5. The anchor assembly tool of claim 4, further comprising a spring attached to the inner member.

6. An anchor assembly tool configured to engage a head member and an anchor defining a recess, comprising:

an outer member having an elongate, tubular main body, a proximal end, a distal end, a longitudinal axis, a lumen extending from the proximal end to the distal end, and an outer member collar disposed on the elongate, tubular main body, the distal end defining a first threaded portion configured to engage the head member, the outer member rotatable about the longitudinal axis;

an inner member having an elongate, tubular main body, a lumen, an inner shaft disposed within the lumen, and an actuator, the main body having a proximal end and a distal end, the inner member movably disposed within the lumen of the outer member, the actuator capable of advancing the inner member within the outer member, the actuator disposed on the proximal end of the main body, the inner shaft having a first position and a second position, the inner member having a radially compressed configuration relative to the longitudinal axis when the inner shaft is in the first position, the inner member having a radially expanded configuration relative to the longitudinal axis when the inner shaft is in the compressed position, the distal end defining a snap-fit structure, the snap-fit structure being configured to engage the anchor; and a handle having a first handle portion and a second handle portion, the first handle portion attached to the outer member, the second handle portion attached to the inner member, the handle having a first configuration and a second configuration;

wherein the distal end of the outer member operates independently from the distal end of the inner member; and wherein activation of the handle from the first configuration to the second configuration moves the inner member a predetermined distance relative to the longitudinal axis.

7. The anchor assembly tool of claim 6, wherein the snap-fit structure comprises a first shaft and a second shaft.

8. The anchor assembly tool of claim 7, wherein the second shaft is disposed substantially opposite the first shaft about the longitudinal axis.

9. The anchor assembly tool of claim 8, wherein the snap-fit structure is movable within the recess of the anchor when the inner shaft is in the first position.

10. The anchor assembly tool of claim 9, wherein the snap-fit structure is not movable within the recess of the anchor when the inner shaft is in the second position.

11. The anchor assembly tool of claim 10, wherein the snap-fit structure rigidly engages the anchor when the inner shaft is in the second position.

12. The anchor assembly tool of claim 7, wherein each of the first and second shafts defines a protrusion and a recess.

13. The anchor assembly tool of claim 6, wherein the inner shaft comprises a main body and a distal portion, the distal portion having a first diameter and the main body having a second diameter; and wherein the second diameter is greater than the first diameter.

* * * * *